(12) United States Patent
Suzuki et al.

(10) Patent No.: US 8,674,117 B2
(45) Date of Patent: Mar. 18, 2014

(54) ORGANOBORON COMPOUND AND METHOD FOR MANUFACTURING THE SAME

(75) Inventors: Hiroki Suzuki, Kanagawa (JP); Sachiko Kawakami, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/334,593

(22) Filed: Dec. 22, 2011

(65) Prior Publication Data

US 2012/0165550 A1 Jun. 28, 2012

(30) Foreign Application Priority Data

Dec. 28, 2010 (JP) ................................. 2010-292993

(51) Int. Cl.
*C07D 495/00* (2006.01)
*C07F 5/02* (2006.01)

(52) U.S. Cl.
USPC ............................................. 549/4; 549/213

(58) Field of Classification Search
USPC ........................................................ 549/4, 213
See application file for complete search history.

(56) References Cited

U.S. PATENT DOCUMENTS

| | | | |
|---|---|---|---|
| 6,525,088 | B1 | 2/2003 | Nagano et al. |
| 8,293,381 | B2 | 10/2012 | Je et al. |
| 2008/0315754 | A1 | 12/2008 | Kawamura et al. |
| 2011/0114928 | A1 | 5/2011 | Suzuki et al. |
| 2011/0168992 | A1* | 7/2011 | Bae et al. ......................... 257/40 |
| 2012/0138914 | A1 | 6/2012 | Kawamura et al. |
| 2012/0165556 | A1 | 6/2012 | Suzuki et al. |

FOREIGN PATENT DOCUMENTS

| | | |
|---|---|---|
| EP | 2 332 931 A2 | 6/2011 |
| JP | 2008-94777 | 4/2008 |
| JP | 2012-503027 | 2/2012 |
| KR | 10-2010-0034719 | 4/2010 |
| WO | WO 2009/069537 A1 | 6/2009 |
| WO | WO 2010/036027 A2 | 4/2010 |
| WO | WO 2010036027 A2 * | 4/2010 |

OTHER PUBLICATIONS

Yao, T., et al. "Synthesis of Polycyclic Aromatics and Heteroaromatics via Electrophilic Cyclization." J. Org. Chem. (2005), 70, pp. 3511-3517.*

Miyaura, N, et al. "Palladium-Catalyzed Cross-Coupling Reactions of Organoboron Compounds." Chem. Rev. (1995), vol. 95, No. 7, pp. 2457-2483.*

Baumgartner, M.T. et al, "The Reactivity of Oxygen Nucleophiles with Aryl Radicals in the $S_{RN}1$ Mechanism," Tetrahedron Letters, vol. 33, No. 17, 1992, pp. 2323-2326.

Baumgartner, M.T. et al, "Photostimulated Reactions of o-Dihalobenzenes with Nucleophiles Derived from the 2-Naphthyl System. Competition Between Electron Transfer, Fragmentation, and Ring Closure Reactions," J. Org. Chem., vol. 58, No. 9, 1993, pp. 2593-2598.

International Search Report for international application PCT/JP2011/079957, mailing date Mar. 13, 2012.

Written Opinion of the International Searching Authority for international application PCT/JP2011/079957, mailing date Mar. 13, 2012.

Kawamura, M. et al., "Accession No. 2010:1493416 / Document No. 154:21579," 2013, STN International HCAPLUS database.

Goldfinger et al, "Directed Electrophilic Cyclizations: Efficient Methodology for the Synthesis of Fused Polycyclic Aromatics," J. Am. Chem. Soc., vol. 119, No. 20, 1997, pp. 4578-4593.

* cited by examiner

*Primary Examiner* — Andrew D Kosar
*Assistant Examiner* — John S Kenyon
(74) *Attorney, Agent, or Firm* — Husch Blackwell LLP

(57) ABSTRACT

To provide a novel organoboron compound which is useful as a reactant of organic synthesis. To provide a method for manufacturing the organoboron compound. A novel organoboron compound represented by General Formula (G1) below is provided. Note that in General Formula (G1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. Further, X represents an oxygen atom or a sulfur atom.

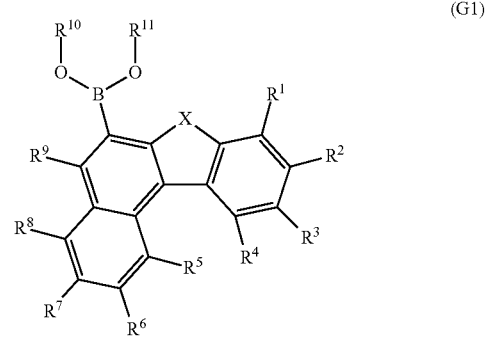

(G1)

15 Claims, 2 Drawing Sheets

ORGANOBORON COMPOUND AND METHOD FOR MANUFACTURING THE SAME

TECHNICAL FIELD

The present invention relates to an organoboron compound and a method for manufacturing the same.

BACKGROUND ART

Organic compounds can take a wide variety of structures compared with inorganic compounds, and have a possibility to provide materials having various functions with appropriate molecular design. For these advantages, materials of organoboron compounds that can be used as synthetic intermediates of various organic compounds have been developed.

For example, Patent Document 1 discloses a material for a light-emitting element synthesized using a benzofuran compound which is converted into organoboron as a material.

For great variations of medical or agricultural chemicals, physiological active substances, materials for light-emitting elements as final products, or the like, there are desirably wide variations of organoboron compounds that can be used as synthetic intermediates thereof. Further, it is desirable in regard to the synthesis of organic compounds to obtain objects with higher purity in a simple manner, and various methods have been thus made. The means for obtaining the objects with high purity in a simple manner include the adoption of a synthesis route using materials which are more stable and easy to purify, the adoption of a synthesis route through which by-products are less likely to be synthesized, and the like.

In addition, while organic compounds are able to be synthesized in a variety of ways, the synthesis often involves multiple synthesis steps. Therefore, the more complex the synthesis method is, the more materials and time are consumed. Accordingly, the proposal of simpler synthesis methods has been desired.

REFERENCE

Patent Document

[Patent Document 1] Japanese Published Patent Application No. 2008-94777

DISCLOSURE OF INVENTION

It is an object of an embodiment of the present invention to provide a novel organoboron compound which is useful as a reactant of organic synthesis.

It is another object of an embodiment of the present invention to provide a method for manufacturing the organoboron compound.

One embodiment of the present invention is an organoboron compound represented by General Formula (G1) below.

[Chemical Formula 1]

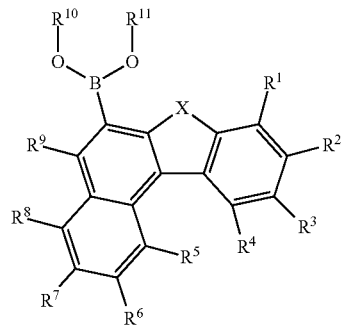

(G1)

Note that in General Formula (G1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. Further, X represents an oxygen atom or a sulfur atom.

Another embodiment of the present invention is a method for manufacturing an organoboron compound represented by General Formula (G1) below which is synthesized in such a manner that a benzo[b]naphtho[1,2-d]furan compound or a benzo[b]naphtho[1,2-d]thiophene compound is converted into organoboron with use of an alkyllithium reagent and a boron reagent.

[Chemical Formula 2]

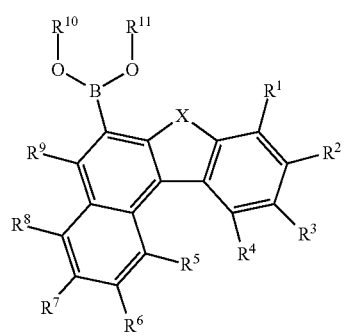

(G1)

Note that in General Formula (G1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. Further, X represents an oxygen atom or a sulfur atom.

Another embodiment of the present invention is an organoboron compound represented by General Formula (G2) below.

[Chemical Formula 3]

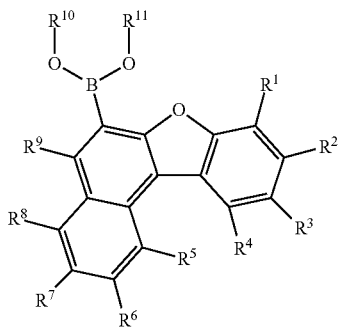

(G2)

Note that in General Formula (G2), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring.

Another embodiment of the present invention is an organoboron compound represented by General Formula (G3) below.

[Chemical Formula 4]

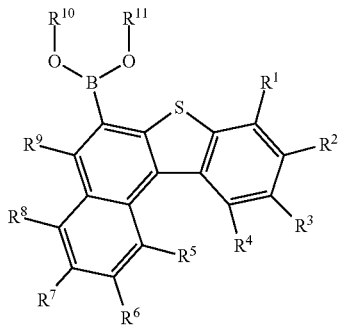

(G3)

Note that in General Formula (G3), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring.

According to an embodiment of the present invention, a novel organoboron compound and a method for manufacturing the same can be provided. The organoboron compound is useful as a reactant of organic synthesis, and a variety of organic compounds can be synthesized using the organoboron compound as a synthetic intermediate.

BRIEF DESCRIPTION OF DRAWINGS

In the accompanying drawings.

BEST MODE FOR CARRYING OUT THE INVENTION

Figure 1A:
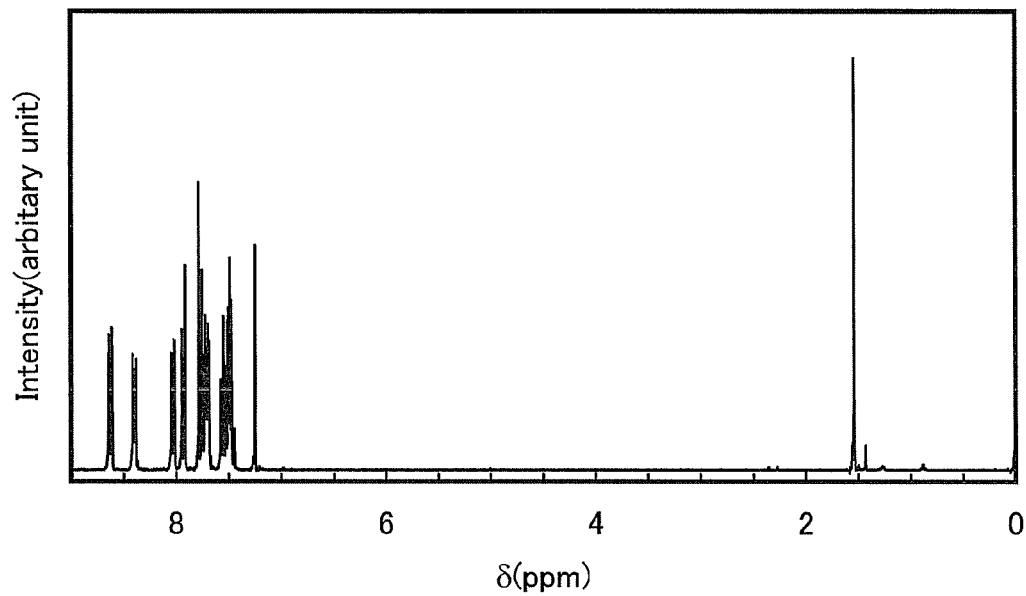
FIGS. 1A and 1B show a result of NMR measurement of benzo[b]naphtho[1,2-d]furan.

Hereinafter, embodiments of the present invention will be described in detail. Note that the present invention is not limited to the following description because it will be easily understood by those skilled in the art that various changes and modifications can be made without departing from the spirit and scope of the present invention. Accordingly, the present invention should not be interpreted as being limited to the description of the embodiments and examples below.

Embodiment 1

In this embodiment, an organoboron compound according to one embodiment of the present invention will be described.

The organoboron compound according to one embodiment of the present invention is represented by General Formula (G1) below.

[Chemical Formula 5]

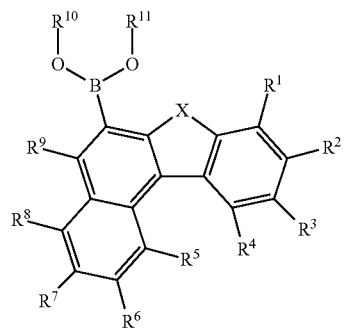

(G1)

In General Formula (G1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. Further, X represents an oxygen atom or a sulfur atom.

Note that in this specification or the like, an organoboron compound represented by any of General Formula (G1) to General Formula (G3) also includes boronic acid. In the case of boronic acid, $R^{10}$ and $R^{11}$ in each of General Formulae (G1) to (G3) represent hydrogen. Note that the boronic acid may be protected by alcohol, ethylene glycol or the like, and in this case, $R^{10}$ and $R^{11}$ in each of General Formulae (G1) to (G3) represent an alkyl group having 1 to 6 carbon atoms.

As specific structures of $R^1$ to $R^9$, hydrogen, a methyl group, an ethyl group, a propyl group, an isopropyl group, a butyl group, a sec-butyl group, an isobutyl group, a tert-butyl group, a phenyl group, a 1-naphthyl group, a 2-naphthyl group, a 2-anthryl group, a 9-anthryl group, a pylen-1-yl group, a pylen-4-yl group, a fluoren-2-yl group and the like can be given. Note that a phenyl group, a 1-naphthyl group, a 2-naphthyl group, a 2-anthryl group, a 9-anthryl group, a pylen-1-yl group, a pylen-4-yl group, or a fluoren-2-yl group, which is an aryl group, may have an alkyl group having 1 to 6 carbon atoms, an aryl group having 6 to 16 carbon atoms, or an aryl group having 6 to 13 carbon atoms as a substituent.

As specific structures of $R^{10}$ and $R^{11}$, hydrogen, a methyl group, an ethyl group, a propyl group, an isopropyl group, a butyl group, a sec-butyl group, an isobutyl group, and a tert-butyl group, a pentyl group, a hexyl group, a cyclopentyl group, a cyclohexyl group and the like can be given. Note that $R^{10}$ and $R^{11}$ may be bonded to each other to form a ring as illustrated in General Formulae (G1-1) to (G1-3) below.

[Chemical Formula 6]

(G1-1)

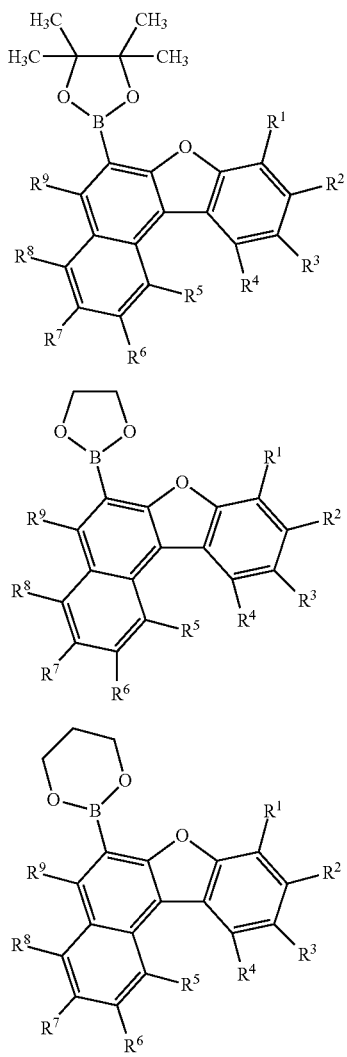

(G1-2)

(G1-3)

In General Formula (G1), X represents an oxygen atom or a sulfur atom. In other words, an organoboron compound represented by General Formula (G1) is an organoboron compound represented by General Formula (G2) or General Formula (G3) below.

[Chemical Formula 7]

(G2)

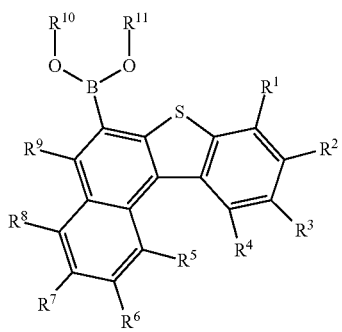

Note that in General Formula (G2), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded to each other to form a ring.

[Chemical Formula 8]

(G3)

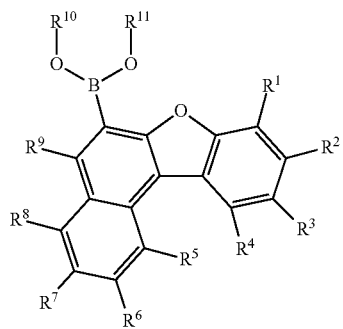

Note that in General Formula (G3), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded to each other to form a ring.

Specific examples of the organoboron compound represented by General Formula (G1) include organoboron compounds represented by Structural Formulae (100) to (143) and (200) to (243). However, the present invention is not limited thereto.

[Chemical Formula 9]

(100)

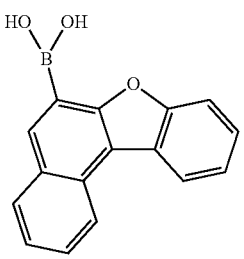

(101)

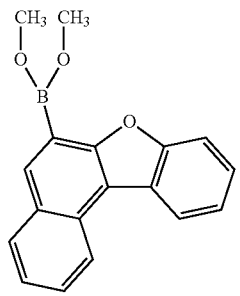

[Chemical Formula 10]
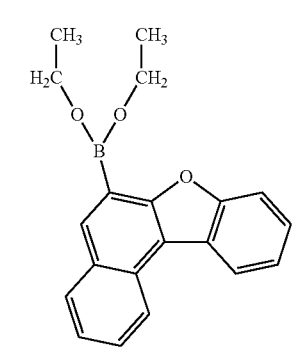 (102)
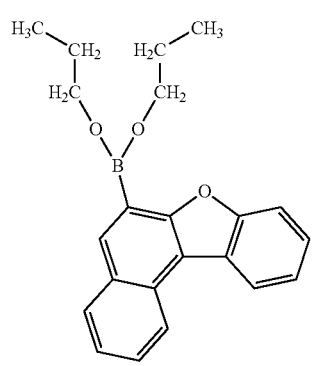 (103)
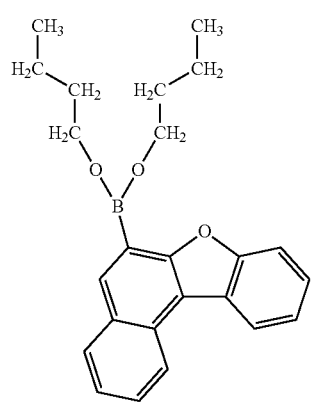 (104)
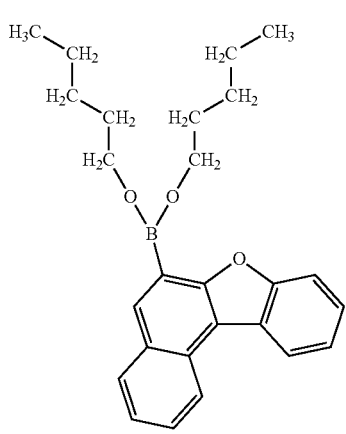 (105)
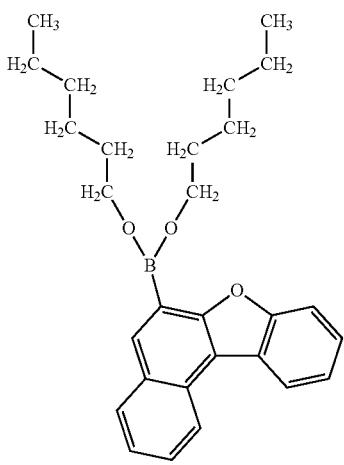 (106)
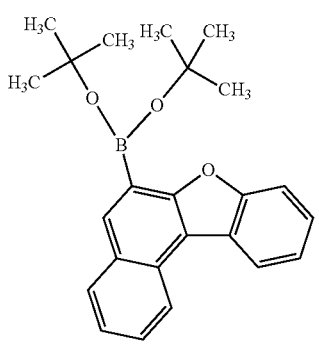 (107)
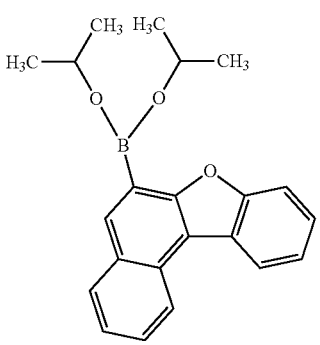 (108)
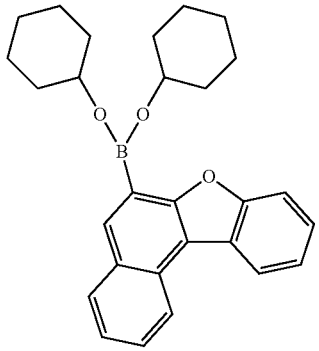 (109)

(110)
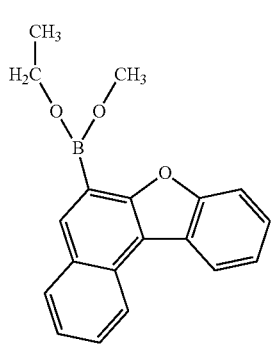
(111)
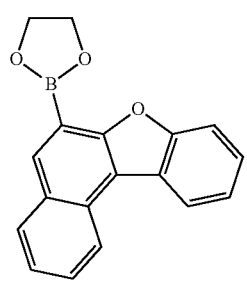
[Chemical Formula 11]
(112)
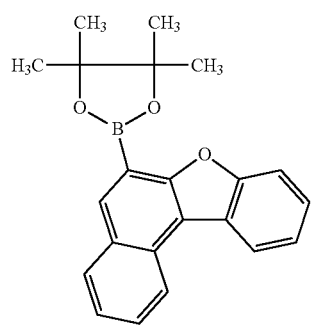
(113)
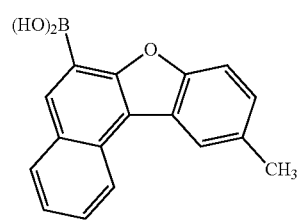
(114)
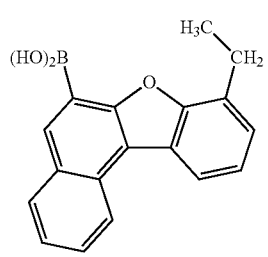
(115)
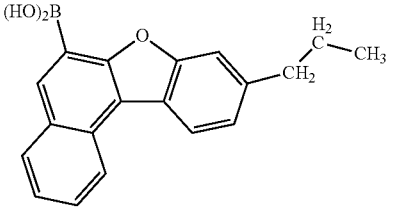
(116)
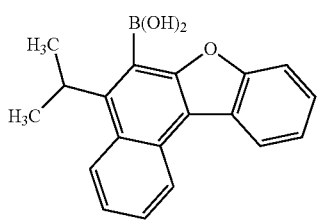
(117)
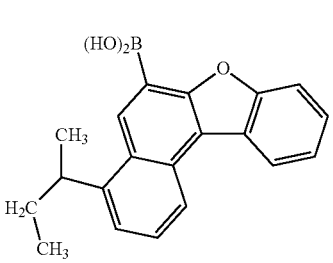
[Chemical Formula 12]
(118)
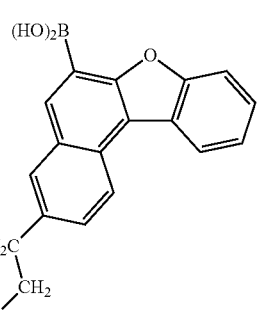
(119)
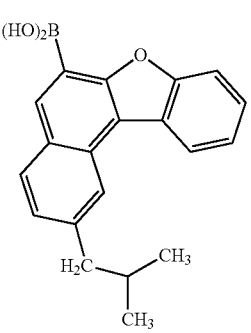

-continued
(120)
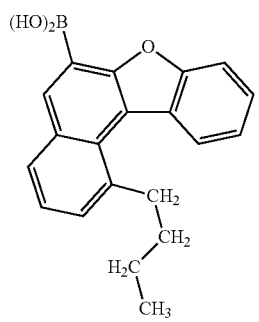
(121)
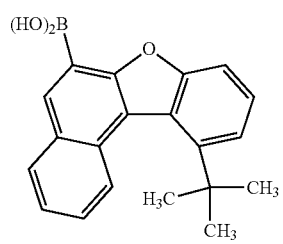
(122)
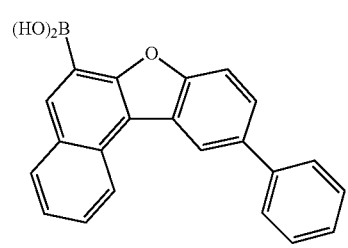
(123)
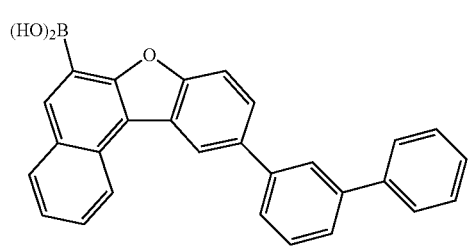
[Chemical Formula 13]
(124)
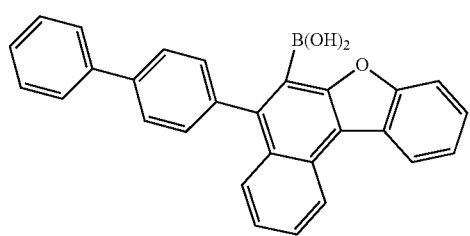
(125)
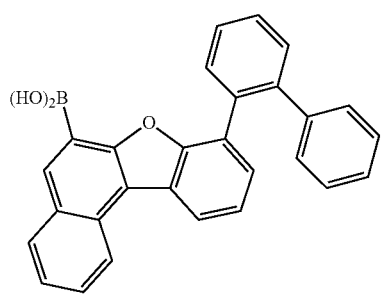
-continued
(126)
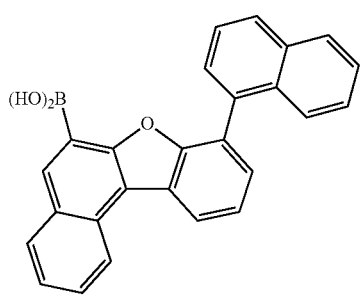
(127)
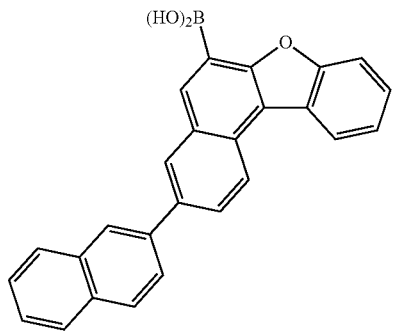
(128)
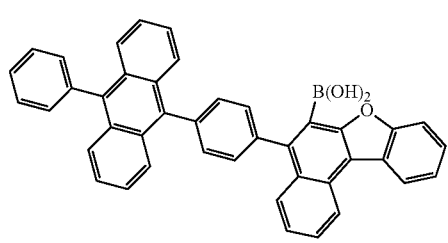
(129)
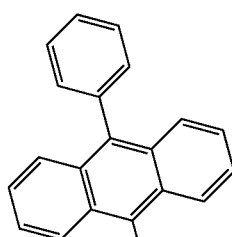
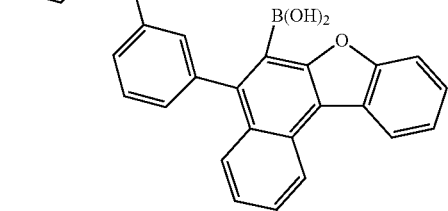
[Chemical Formula 14]
(130)
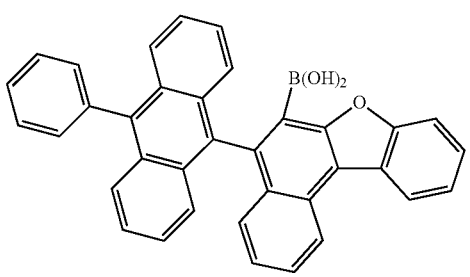

(131)
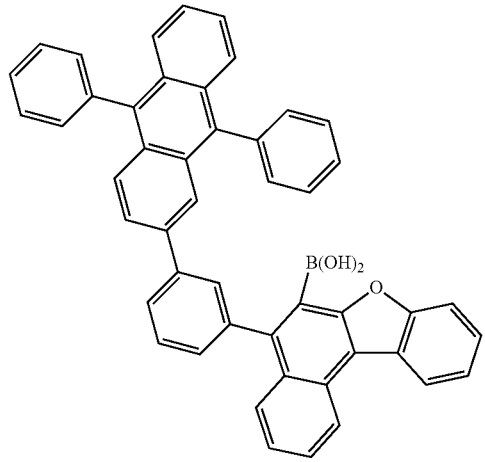
(132)
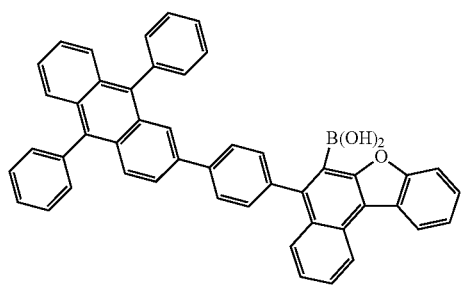
(133)
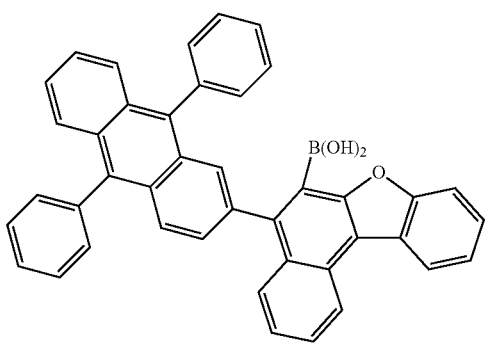
(134)
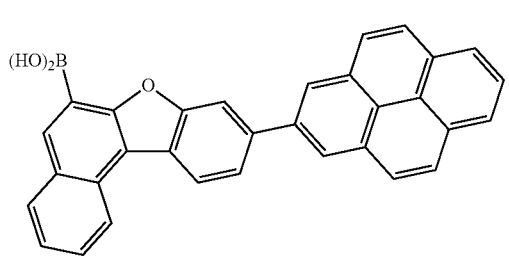
(135)
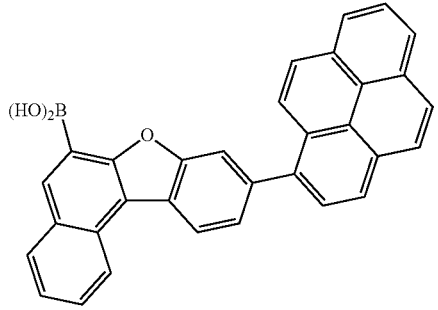
[Chemical Formula 15]
(136)
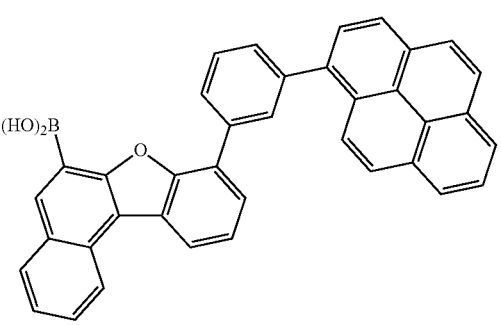
(137)
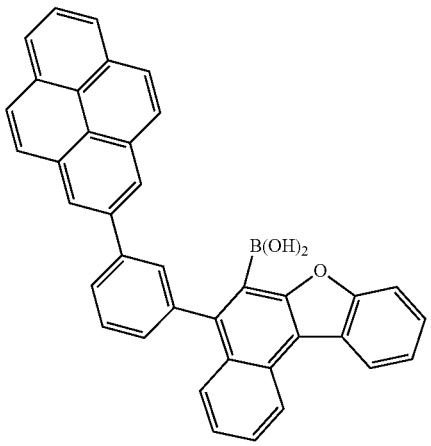
(138)
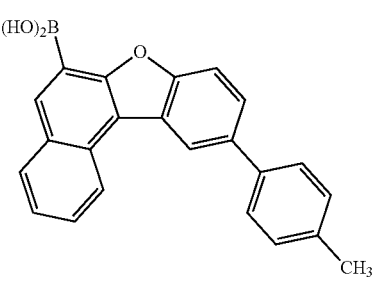

[Chemical Formula 16]
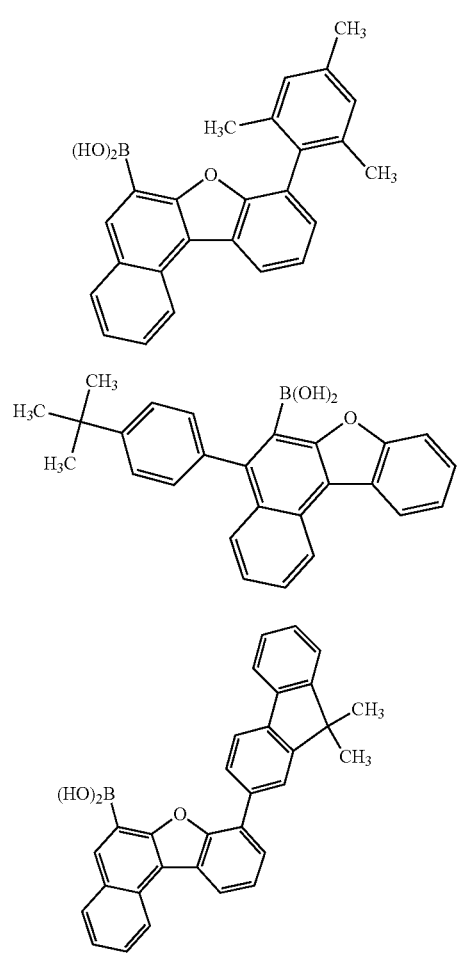
(139)
(140)
(141)
(142)
(143)
[Chemical Formula 17]
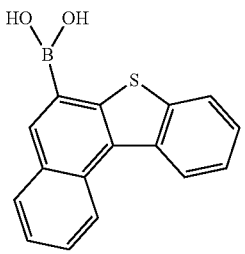
(200)
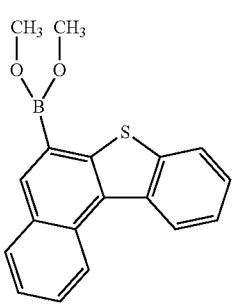
(201)
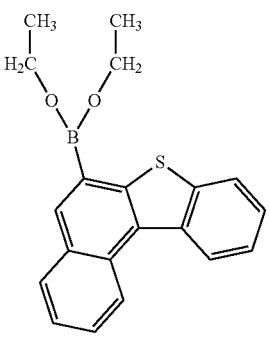
(202)
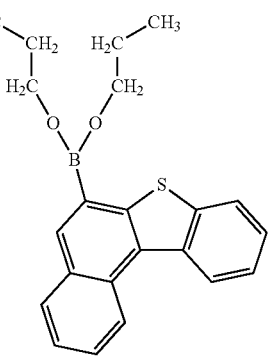
(203)

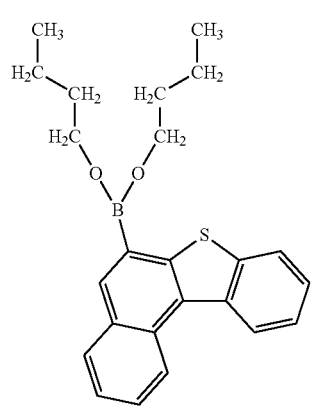
(204)
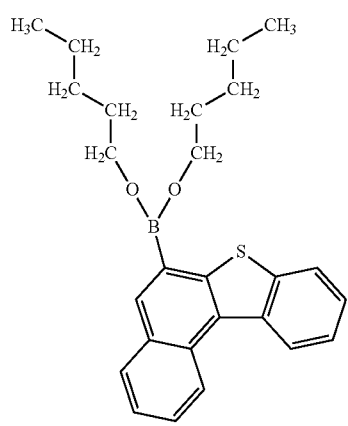
(205)
[Chemical Formula 18]
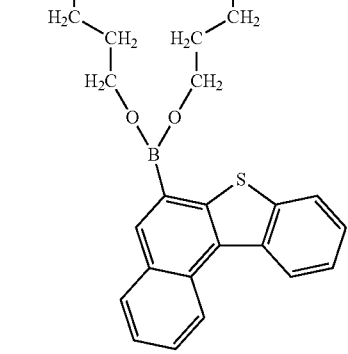
(206)
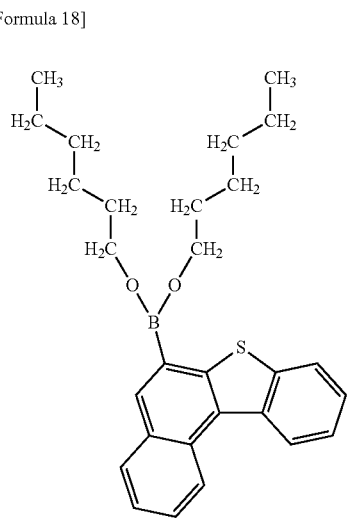
(207)
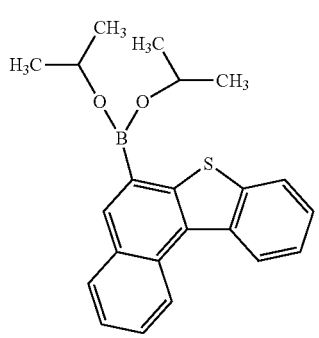
(208)
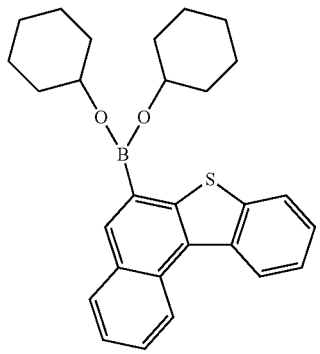
(209)
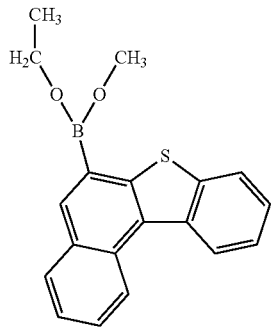
(210)
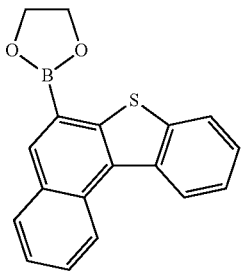
(211)
[Chemical Formula 19]
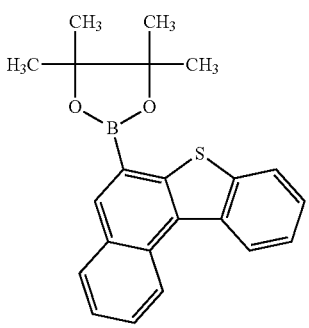
(212)

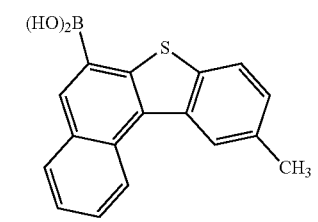 (213)
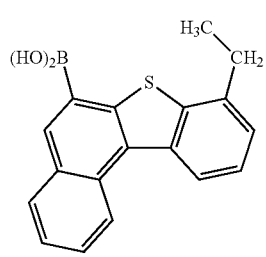 (214)
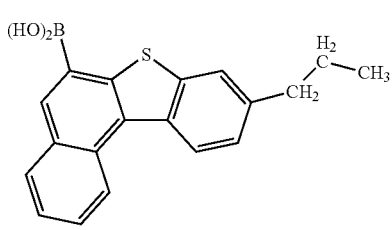 (215)
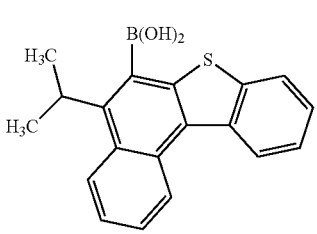 (216)
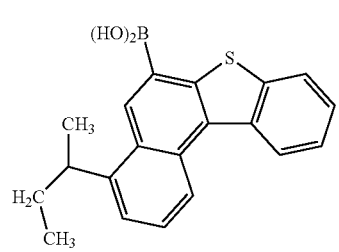 (217)
[Chemical Formula 20]
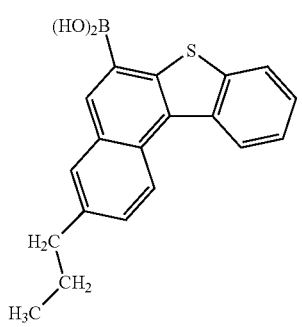 (218)
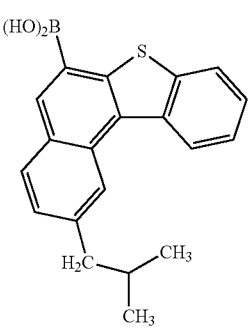 (219)
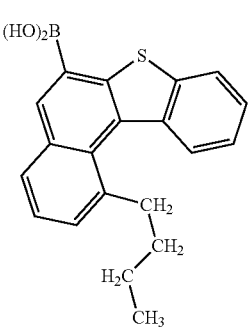 (220)
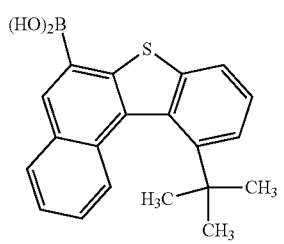 (221)
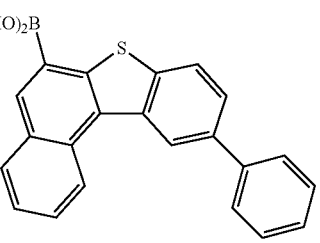 (222)
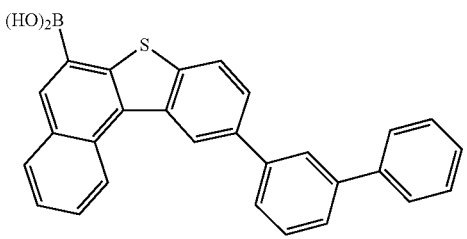 (223)
[Chemical Formula 21]
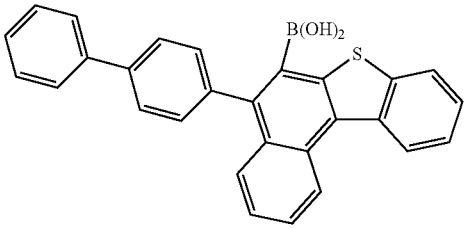 (224)

(225)
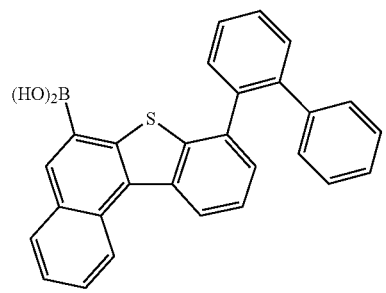
(226)
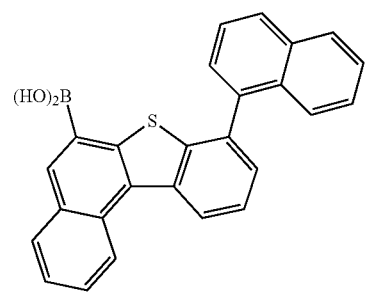
(227)
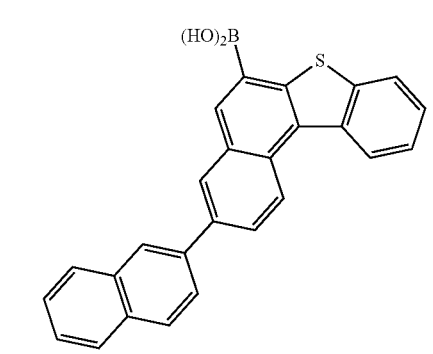
(228)
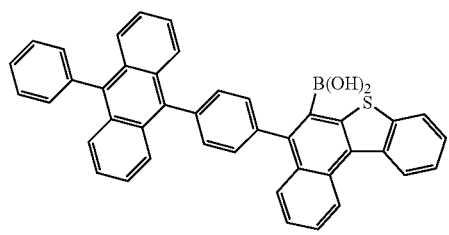
(229)
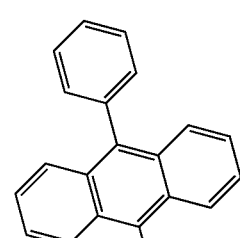
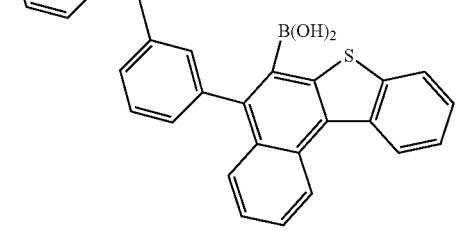
[Chemical Formula 22]
(230)
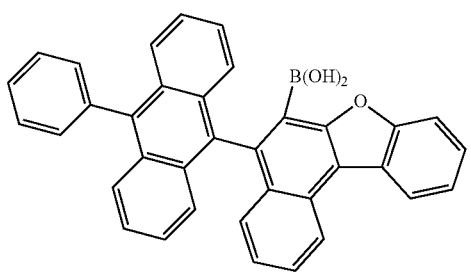
(231)
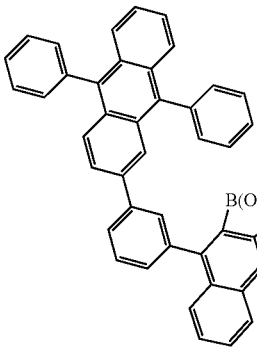
(232)
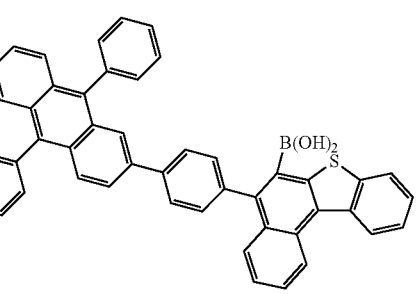
(233)
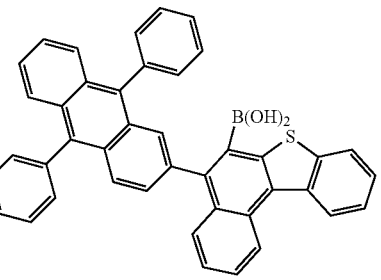
(234)
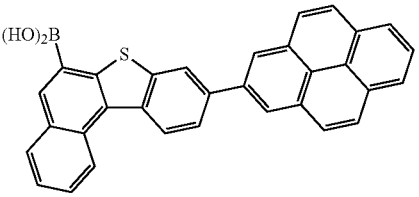

(235)
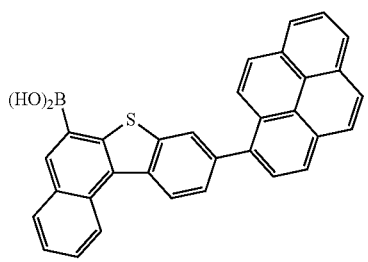
[Chemical Formula 23]
(236)
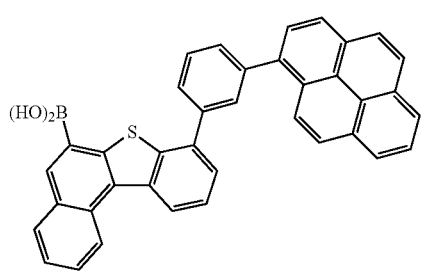
(237)
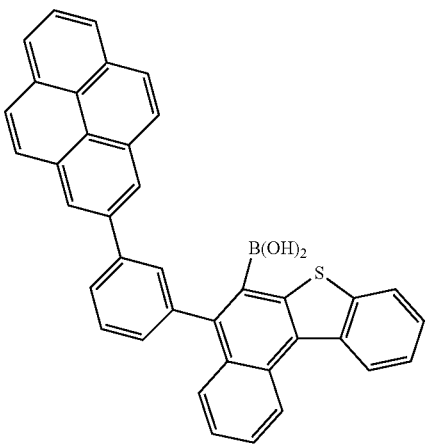
(238)
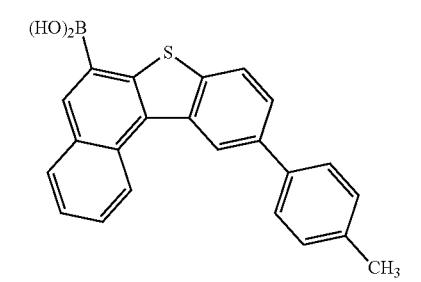
(239)
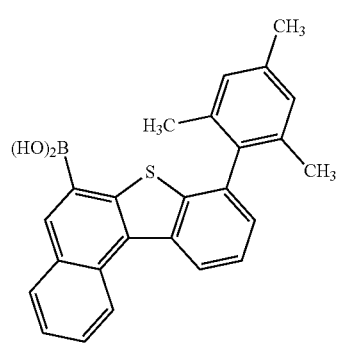
(240)
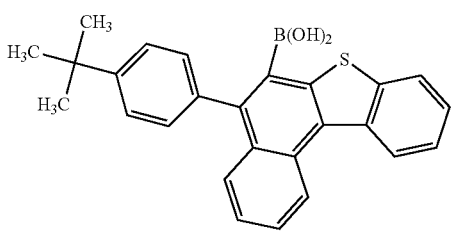
(241)
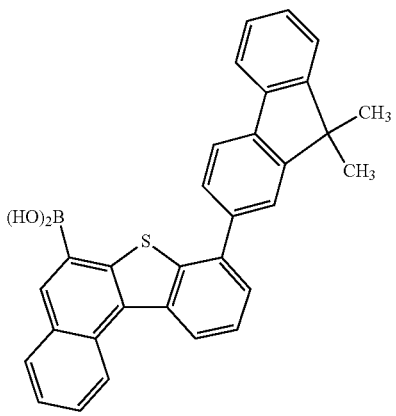
[Chemical Formula 24]
(242)
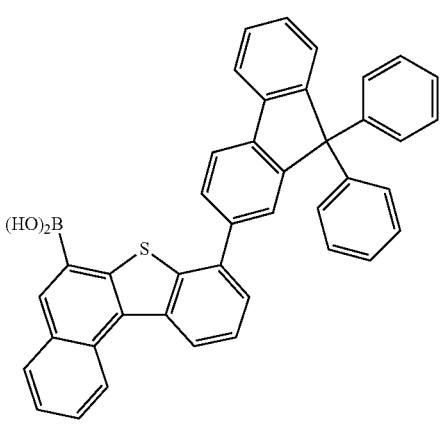
(243)
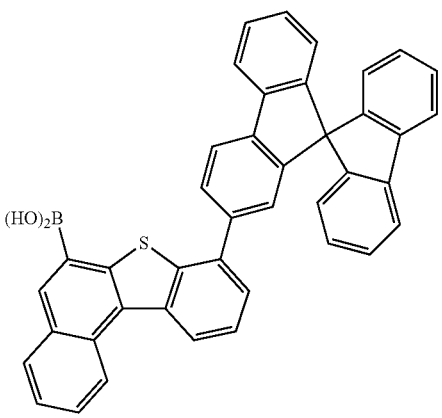
A variety of reactions can be applied to the method for synthesizing the organoboron compound represented by General Formula (G1). For example, synthesis reactions described below enable the synthesis of the organoboron compound represented by General Formula (G1). Note that the method for synthesizing the organoboron compound represented by General Formula (G1) which is one embodiment of the present invention is not limited to the following one.

A benzo[b]naphtho[1,2-d]furan compound or a benzo[b]naphtho[1,2-d]thiophene compound is converted into organoboron with use of an alkyllithium reagent and a boron reagent, whereby the organoboron compound in this embodiment can be manufactured. An example of reaction is described below.

As illustrated in Synthesis Scheme (A-1), a benzo[b]naphtho[1,2-d]furan compound or a benzo[b]naphtho[1,2-d]thiophene compound (a1) is converted into organoboron with use of an alkyllithium reagent and a boron reagent, whereby the organoboron compound represented by General Formula (G1) can be obtained. Note that in Synthesis Scheme (A-1), the 6-position of the benzo[b]naphtho[1,2-d]furan compound or the benzo[b]naphtho[1,2-d]thiophene compound (a1) is selectively converted into organoboron.

[Chemical Formula 25]

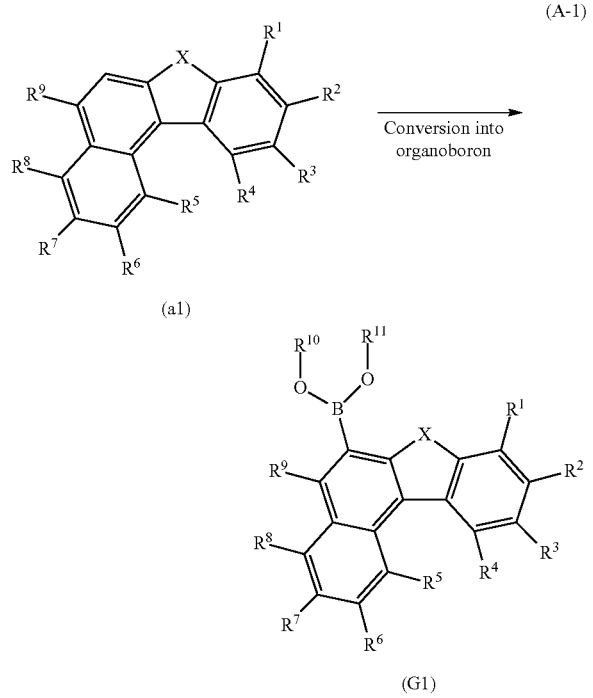

In Synthesis Scheme (A-1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. Further, X represents an oxygen atom or a sulfur atom.

Note that in this specification or the like, the conversion of the benzo[b]naphtho[1,2-d]furan compound or the benzo[b]naphtho[1,2-d]thiophene compound (a1) illustrated in Synthesis Scheme (A-1) into organoboron includes the conversion into boronic acid. In the case of the conversion into boronic acid, $R^{10}$ and $R^{11}$ in each of General Formulae (G1) to (G3) represent hydrogen. Note that the boronic acid may be protected by ethylene glycol or the like. In this case, $R^{10}$ and $R^{11}$ in each of General Formulae (G1) to (G3) represent an alkyl group having 1 to 6 carbon atoms.

In Synthesis Scheme (A-1), an ether-based solvent or the like such as diethyl ether, tetrahydrofuran (THF), or cyclopentyl methyl ether can be used. Further, the alkyllithium reagent may be n-butyllithium, sec-butyl lithium, tert-butyl lithium, or the like. Furthermore, addition of a coordinating additive to such an alkyllithium reagent can enhance reactivity. The coordinating additive that can be used may be tetramethylethylenediamine (TMEDA) or the like. In addition, the boron reagent may be trimethyl borate, triisopropyl borate, or the like.

Thus, the organoboron compound represented by General Formula (G1) can be synthesized. In the reaction illustrated in Synthesis Scheme (A-1), the 6-position of the benzo[b]naphtho[1,2-d]furan compound or the benzo[b]naphtho[1,2-d]thiophene compound (a1) can be selectively converted into organoboron, in which by-products are less likely to be synthesized. Further, the reaction illustrated in Synthesis Scheme (A-1) has a small number of reaction steps, which is simple. Accordingly, the organoboron compound represented by General Formula (G1) that is an objective substance can be synthesized with high purity.

The organoboron compound represented by General Formula (G1) is useful as a reactant of organic synthesis, and a variety of organic compounds can be synthesized using the organoboron compound as a synthetic intermediate.

Embodiment 2

In this embodiment, a method for synthesizing the benzo[b]naphtho[1,2-d]furan compound that can be used as a material of the organoboron compound described in Embodiment 1 will be described. Note that the method for synthesizing the benzo[b]naphtho[1,2-d]furan compound that can be used as the material of the organoboron compound described in Embodiment 1 is not limited to the following one.

[Synthesis Method 1]

As illustrated in Synthesis Scheme (B-1), a β-naphthol derivative (b1) is coupled with an organoboron compound of an aryl derivative (b2) by the Suzuki-Miyaura coupling using a palladium catalyst, whereby a β-naphthol derivative having a halogen group (b3) can be obtained.

[Chemical Formula 26]

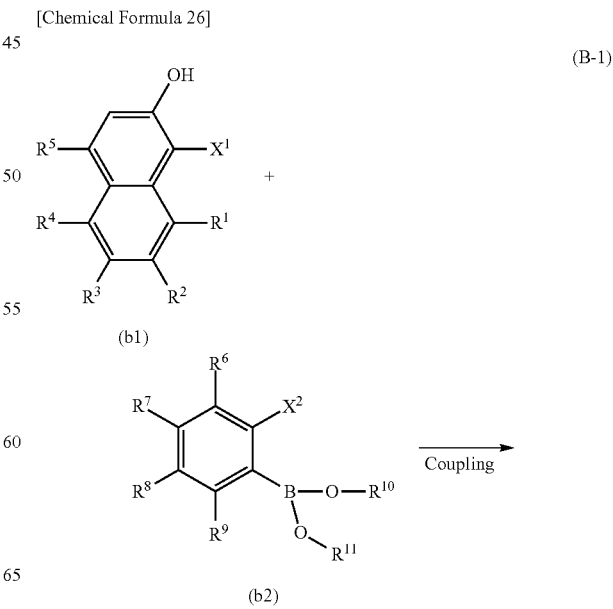

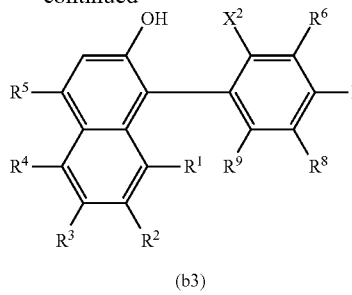

(b3)

In Synthesis Scheme (B-1), $R^1$ to $R^9$ separately represent any one of hydrogen, an alkyl group having 1 to 6 carbon atoms, and an aryl group having 6 to 16 carbon atoms. $R^{10}$ and $R^{11}$ separately represent hydrogen or an alkyl group having 1 to 6 carbon atoms, and $R^{10}$ and $R^{11}$ may be bonded with each other to form a ring. $X^1$ represents halogen or a triflate group. In the case where $X^1$ is halogen, in particular, bromine or iodine is preferable. Further, $X^2$ represents halogen, preferably chlorine, iodine, or bromine, more preferably, fluorine.

Note that in Synthesis Scheme (B-1), the organoboron compound of an aryl derivative (b2) includes boronic acid. In the case of boronic acid, $R^{10}$ and $R^{11}$ in the organoboron compound of an aryl derivative (b2) represent hydrogen. Note that the boronic acid may be protected by ethylene glycol or the like. In this case, $R^{10}$ and $R^{11}$ in the organoboron compound of an aryl derivative (b2) represent an alkyl group having 1 to 6 carbon atoms.

Examples of palladium catalysts that can be used in Synthesis Scheme (B-1) include palladium(II) acetate, tetrakis(triphenylphosphine)palladium(0), and the like. Examples of ligands of the palladium catalyst that can be used in Synthesis Scheme (B-1) include tri(ortho-tolyl)phosphine, triphenylphosphine, tricyclohexylphosphine, and the like. In addition, examples of the base that can be used include organic bases such as sodium tert-butoxide, and inorganic bases such as a potassium carbonate and a sodium carbonate. Examples of solvents that can be used are as follows: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Use of a mixed solvent of toluene and water or a mixed solvent of toluene, ethanol, and water is more preferable.

Note that the case where a halogen group $X^1$ of the β-naphthol derivative (b1) is reacted with a boron compound group of the organoboron compound of an aryl derivative (b2) is illustrated in Synthesis Scheme (B-1); however, also by coupling a boron compound of the β-naphthol derivative (b1) with a halide of the organoboron compound of an aryl derivative (b2) using the Suzuki-Miyaura coupling, the β-naphthol derivative having a halogen group (b3) can be obtained.

Next, the β-naphthol derivative having a halogen group (b3) is intramolecularly cyclized by formation of an ether bond according to a Williamson ether synthesis to form a benzo[b]naphtho[1,2-d]furan ring, so that a benzo[b]naphtho[1,2-d]furan compound (b4) can be obtained.

[Chemical Formula 27]

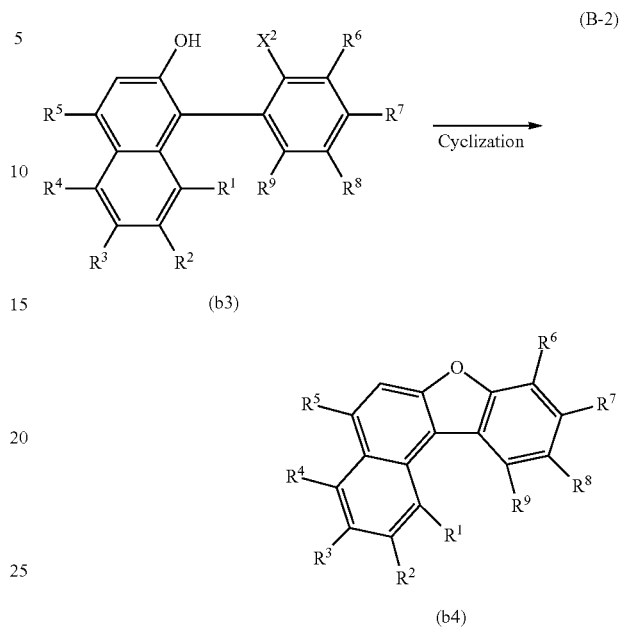

Examples of the base that can be used in Synthesis Scheme (B-2) include inorganic bases such as sodium hydride, potassium carbonate, potassium hydroxide, and the like. In addition, a salt such as sodium iodide may be added to the bases described above. Examples of the solvent that can be used include aprotic polar solvents such as acetonitrile, N,N-dimethylformamide (DMF), dimethyl sulfoxide (DMSO), and N-methyl-pyrrolidone (NMP) and ketones such as cyclohexanone and 2-butanone, and acetone.

Further, a method for synthesizing the benzo[b]naphtho[1,2-d]furan compound according to this embodiment, which is different from Synthesis Method 1, will be described below as Synthesis Method 2.

[Synthesis Method 2]

As illustrated in Synthesis Scheme (C-1), a naphthalene derivative having an alkoxide group (c1) is coupled with an organoboron compound of an aryl derivative (c2) by the Suzuki-Miyaura coupling using a palladium catalyst, whereby an alkoxide compound of a naphthalene derivative (c3) can be obtained.

[Chemical Formula 28]

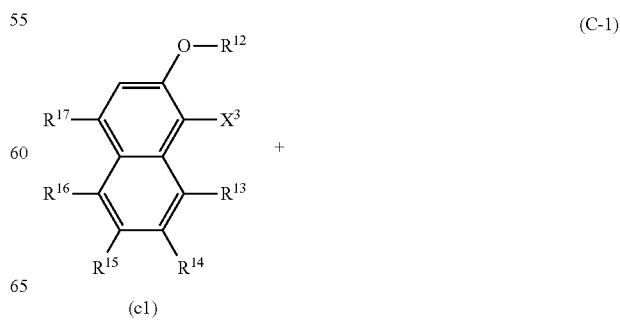

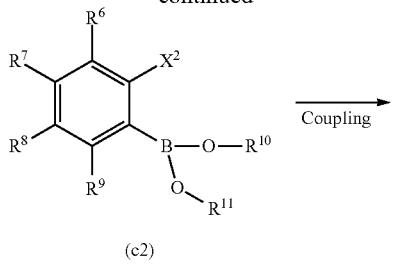

(c2)

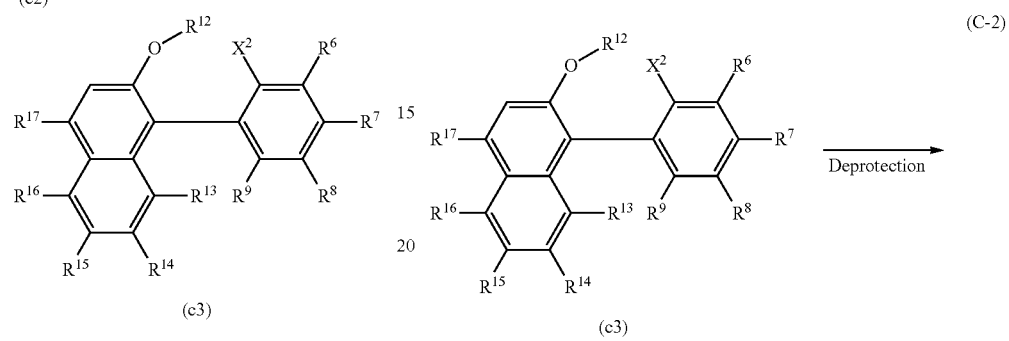

In Synthesis Scheme (C-1), $R^{12}$ represents an alkyl group having 1 to 6 carbon atoms. Further, $R^{13}$ to $R^{17}$ separately represent any one of hydrogen, an alkyl group having 1 to 6 carbon atoms, and an aryl group having 6 to 16 carbon atoms. Furthermore, $X^3$ represents a halogen or a triflate group. In the case where $X^3$ is a halogen, in particular, chlorine, bromine, or iodine is preferable.

Examples of palladium catalysts that can be used in Synthesis Scheme (C-1) include palladium(II) acetate, tetrakis(triphenylphosphine)palladium(0), and the like. Examples of ligands of the palladium catalyst that can be used in Synthesis Scheme (C-1) include tri(ortho-tolyl)phosphine, triphenylphosphine, tricyclohexylphosphine, and the like. In addition, examples of the base that can be used include organic bases such as sodium tert-butoxide, and inorganic bases such as a potassium carbonate and a sodium carbonate. Examples of solvents that can be used are as follows: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Use of a mixed solvent of toluene and water or a mixed solvent of toluene, ethanol, and water is more preferable.

Note that the case where a halogen group $X^3$ of the naphthalene derivative (c1) is reacted with a boron compound group of the organoboron compound of an aryl derivative (c2) is illustrated in Synthesis Scheme (C-1); however, also by coupling a boron compound of the naphthalene derivative (c1) with a halide of the organoboron compound of an aryl derivative (c2) using the Suzuki-Miyaura coupling, the alkoxide compound of a naphthalene derivative (c3) can be obtained.

In the reaction illustrated in Synthesis Scheme (C-1), the naphthalene derivative (c1) having an alkoxide group is used instead of the β-naphthol derivative (b1) in Synthesis Scheme (B-1) described above. By use of the naphthalene derivative having an alkoxide group (c1), a hydroxyl group in the β-naphthol derivative (b1) can be protected; accordingly, introduction of a substituent into the β-naphthol derivative having a halogen group (b3) can be performed more easily.

Next, as illustrated in Synthesis Scheme (C-2), the alkoxide compound of a naphthalene derivative (c3) is deprotected with a Lewis acid, whereby a β-naphthol derivative having a halogen group (c4) can be obtained.

[Chemical Formula 29]

As the Lewis acid that can be used in Synthesis Scheme (C-2), boron tribromide, trimethyliodosilane, or the like is preferred when $R^{12}$ is a methyl group. Alternatively, trifluoroacetic acid, a 4 mol/L hydrochloric acid.ethyl acetate solution or the like is preferred when $R^{12}$ is a tert-butyl group. Further, examples of the solvent that can be used include halogen-based solvents such as dichloromethane, chloroform, and carbon tetrachloride, and aromatic hydrocarbon-based solvents such as toluene and xylene.

Since the subsequent step in Synthesis Scheme (C-2) can be performed in a manner similar to that of Synthesis Scheme (B-2) described above, detailed description thereof is omitted.

Thus, the benzo[b]naphtho[1,2-d]furan compound (b4) can be synthesized. The benzo[b]naphtho[1,2-d]furan compound (b4) described in this embodiment can be used as a material for synthesizing the organoboron compound described in Embodiment 1.

Example 1

In this example, Synthesis Example 1 and Synthesis Example 2, in each of which benzo[b]naphtho[1,2-d]furan-6-boronic acid represented by Structural Formula (100) in Embodiment 1 was manufactured, will be described.

[Chemical Formula 30]

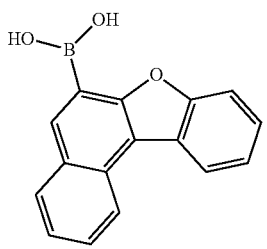

(100)

Synthesis Example 1

[Step 1] Synthesis of 1-(2-Fluorophenyl)-2-naphthol

Into a 200 mL three-neck flask were placed 1.4 g (10 mmol) of 2-fluorobenzeneboronic acid, 2.2 g (10 mmol) of 1-bromo-2-naphthol, 153 mg (0.5 mmol) of tri(o-tolyl)phosphine, 25 mL of toluene, 25 mL of ethanol, and 5.0 mL of a 2M aqueous solution of potassium carbonate. This mixture was degassed under reduced pressure, and the air in the system was replaced with nitrogen. This mixture was stirred at 80° C., 23 mg (0.1 mmol) of palladium(II) acetate was added thereto, and the mixture was refluxed at about 100° C. for 6.5 hours. After the reflux, this mixture was washed with water, and the aqueous layer was subjected to extraction with ethyl acetate. The obtained solution of the extract and the organic layer were combined and washed with saturated brine. The obtained organic layer was dried with magnesium sulfate. This mixture was gravity-filtered, and the obtained filtrate was concentrated to give a brown oily substance. This oily substance was purified by silica gel column chromatography (developing solvent: toluene), so that 1.6 g of a brown oily substance of the object of the synthesis was obtained in 69% yield. The reaction scheme of Step 1 is illustrated in (E1-1).

[Chemical Formula 31]

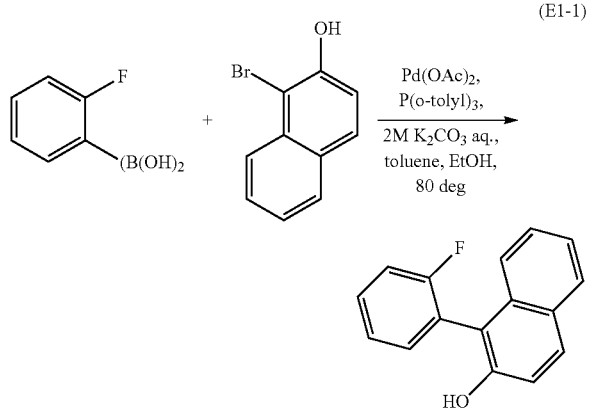

(E1-1)

[Step 2] Synthesis of Benzo[b]naphtho[1,2-d]furan

Into a 1 L three-neck flask were placed 15 g (63 mmol) of 1-(2-fluorophenyl)-2-naphthol, 300 mL of N-methyl-2-pyrrolidone (NMP), and 18 g (130 mmol) of potassium carbonate. The mixture in this flask was stirred at 150° C. for 6 hours under a nitrogen stream. After that, this mixture was cooled down to room temperature and added to about 500 mL of water. The aqueous layer of this mixture was subjected to extraction with ethyl acetate, and the obtained solution of the extract and the organic layer were combined and washed with water and saturated brine. The organic layer was dried with magnesium sulfate, and after that, this mixture was gravity-filtered. The obtained filtrate was concentrated to give an oily substance. The obtained oily substance was purified by silica gel column chromatography (developing solvent: hexane) to give an oily substance. The obtained oily substance was dried under reduced pressure, so that 11.8 g of a colorless transparent oily substance of the object of the synthesis was obtained in 86% yield. The reaction scheme of Step 2 is illustrated in (E1-2).

[Chemical Formula 32]

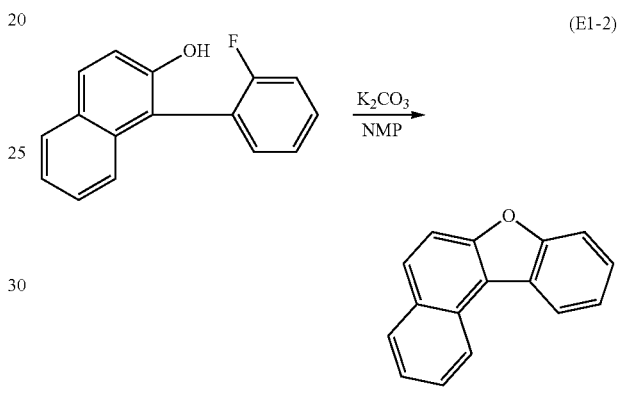

(E1-2)

Nuclear magnetic resonance (NMR) spectroscopy identified this compound as benzo[b]naphtho[1,2-d]furan, which was the object of the synthesis.

$^1$H-NMR data of the obtained compound are as follows:
$^1$H-NMR (CDCl$_3$, 300 MHz): δ=7.44-7.57 (m, 3H), 7.68-7.78 (m, 3H), 7.93 (d, J=9.3 Hz, 1H), 8.03 (d, J=7.8 Hz, 1H), 8.37-8.43 (m, 1H), 8.62 (d, J=8.4 Hz, 1H)

Figure 1B:
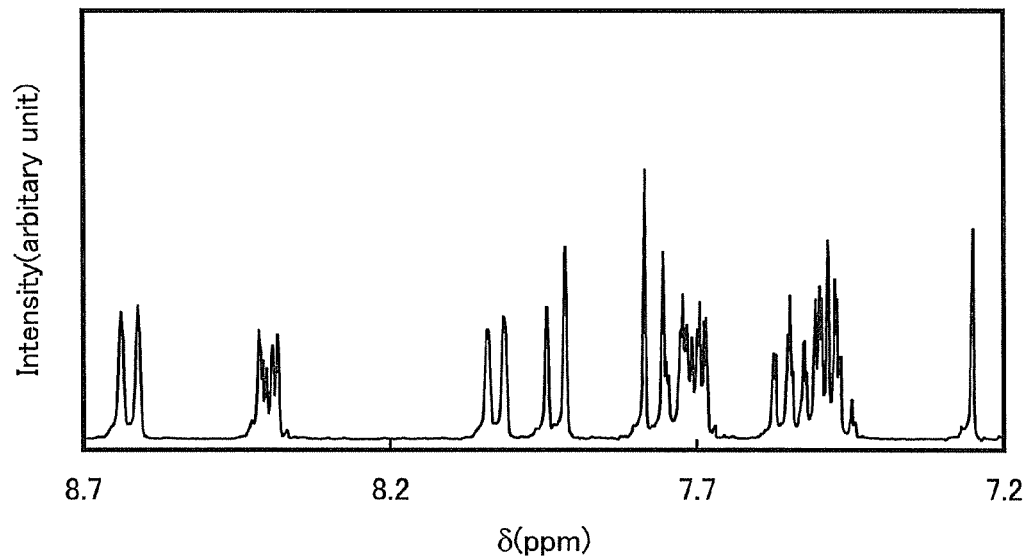

Further, the $^1$H-NMR charts are shown in FIGS. 1A and 1B. Note that FIG. 1B is a chart showing an enlarged part of FIG. 1A in the range of 7.2 ppm to 8.7 ppm.

[Step 3] Synthesis of Benzo[b]naphtho[1,2-d]furan-6-boronic acid

After the air in a 500 mL three-neck flask was replaced with nitrogen, 5.8 g (50 mmol) of tetramethylethylenediamine (TMEDA) and 180 mL of tetrahydrofuran (THF) were placed into the flask, and this solution was cooled to −80° C. Then, 50 mL (50 mmol) of sec-butyl lithium (a 1.0 mol/L solution of cyclohexane and n-hexane) was dripped into this solution with a syringe. After that, this solution was stirred at the same temperature for 30 minutes. Then, 10 g (45 mmol) of benzo[b]naphtho[1,2-d]furan dissolved in 70 mL of THF was added dropwise to this solution with a dropping funnel. After that, this solution was stirred at the same temperature for 2 hours. Then, 11 mL (100 mmol) of trimethyl borate was added to this solution, and the mixture was stirred for 2 days while its temperature was returned to room temperature. After that, the aqueous layer of this mixture was subjected to extraction with ethyl acetate, and the obtained solution of the extract and the organic layer were combined and washed with a saturated aqueous solution of sodium hydrogen carbonate and saturated brine. The organic layer was dried with magnesium sulfate, and after that, this mixture was gravity-filtered. The obtained filtrate was concentrated to give a white solid. A mixed solvent of toluene and hexane was added to the obtained solid, the mixture was irradiated with ultrasonic waves, and a solid was collected by suction filtration, so that 9.2 g of a white powder of the object of the synthesis was obtained in 78% yield. The reaction scheme of Step 3 is illustrated in (E1-3).

[Chemical Formula 33]

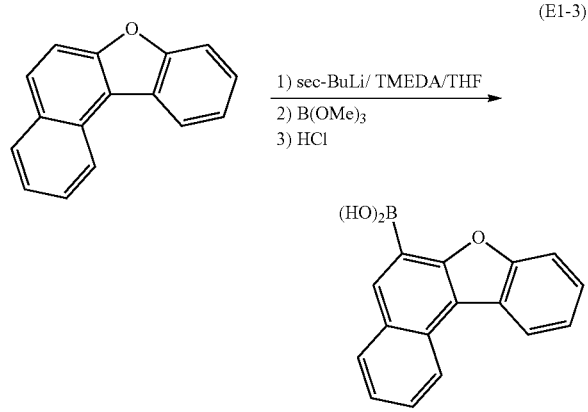

Thus, the benzo[b]naphtho[1,2-d]furan-6-boronic acid represented by Structural Formula (100) can be synthesized.

Synthesis Example 2

In this synthesis example, a synthesis example of the benzo[b]naphtho[1,2-d]furan-6-boronic acid, which is different from Synthesis Example 1 described above, is described.

[Step 1] Synthesis of
1-(2-Fluorophenyl)-2-methoxynaphthalene

Into a 500 mL three-neck flask were placed 8.7 g (35 mmol) of 1-bromo-2-methoxynaphthalene, and 5.0 g (35 mmol) of 2-fluorophenylboronic acid. The air in the flask was replaced with nitrogen. To this mixture were added 120 mL of toluene, 60 mL of ethanol, and 40 mL of an aqueous solution of sodium carbonate (2.0 mol/L). While the pressure was reduced, this mixture was stirred to be degassed. To this mixture was added 2.0 g (1.7 mmol) of tetrakis(triphenylphosphine)palladium(0), and the mixture was stirred at 80° C. for 8 hours under a nitrogen stream. The aqueous layer of the obtained mixture was subjected to extraction with toluene, and the obtained solution of the extract and the organic layer were combined and washed with saturated brine. The organic layer was dried with magnesium sulfate, and this mixture was gravity-filtered. An oily substance obtained by concentration of the obtained filtrate was dissolved in about 30 mL of toluene. This solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). An oily substance obtained by concentration of the obtained filtrate was dried under reduced pressure, so that 5.3 g of a pale yellow oily substance of the object of the synthesis was obtained in 60% yield. The reaction scheme of Step 1 is illustrated in (E2-1).

[Chemical Formula 34]

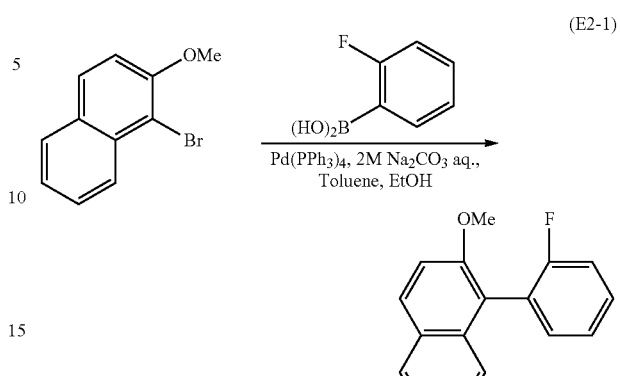

[Step 2] Synthesis of 1-(2-Fluorophenyl)-2-naphthol

Into a 500 mL three-neck flask were placed 5.3 g (21 mmol) of 1-(2-fluorophenyl)-2-methoxynaphthalene and 150 mL of dichloromethane. At 0° C. under a nitrogen stream, 45 mL (45 mmol) of boron tribromide (a 1M dichloromethane solution) was added dropwise to this solution with a dropping funnel. After that, the mixture was stirred at the same temperature for 6 hours. Then, this solution was stirred at room temperature for 2 days. After that, about 100 mL of water was added to this solution, and the solution was stirred for 1 hour. Then, addition of about 100 mL of a saturated aqueous solution of sodium hydrogen carbonate was followed by one-hour stirring. Then, the aqueous layer of this mixture was subjected to extraction with dichloromethane, and the obtained solution of the extract and the organic layer were combined and washed with water and a saturated aqueous solution of sodium hydrogen carbonate. The organic layer was dried with magnesium sulfate. Then, this mixture was gravity-filtered. The obtained filtrate was concentrated to give an oily substance. The obtained oily substance was dried under reduced pressure, so that 4.8 g of a brown solid of the object of the synthesis was obtained in 97% yield. The reaction scheme of Step 2 is illustrated in (E2-2).

[Chemical Formula 35]

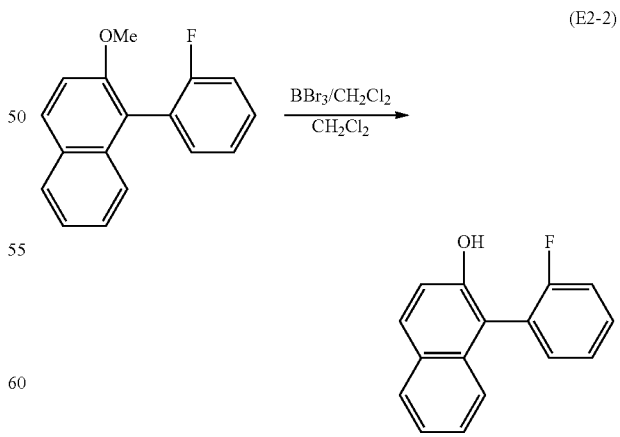

With the use of 1-(2-fluorophenyl)-2-naphthol which was obtained, the same reaction as the reaction scheme (E1-2) and the reaction scheme (E1-3) described in Synthesis Example 1 is performed, whereby the benzo[b]naphtho[1,2-d]furan-6- boronic acid can be synthesized. For details thereof, the description in Synthesis Example 1 can be referred to.

Reference Example 1

In this reference example, a position was specified where the benzo[b]naphtho[1,2-d]furan which was synthesized as an intermediate in each of Synthesis Example 1 and Synthesis Example 2 was converted into boronic acid in the reaction scheme (E1-3). Specifically, 6-phenylbenzo[b]naphtho[1,2-d]furan (abbreviation: PBnf) was synthesized using the compound synthesized in the reaction scheme (E1-3), and was subjected to X-ray crystallography.

Synthesis of 6-phenylbenzo[b]naphtho[1,2-d]furan (abbreviation: PBnf)

Into a 200 mL three-neck flask were placed 0.90 g (5.7 mmol) of bromobenzene and 1.5 g (5.7 mol) of benzo[b]naphtho[1,2-d]furan-6-boronic acid, and the air in the flask was replaced with nitrogen. To this mixture were added 20 mL of toluene, 10 mL of ethanol, and 6.0 mL of an aqueous solution of sodium carbonate (2.0 mol/L). While the pressure was reduced, this mixture was stirred to be degassed. To this mixture was added 0.33 g (0.28 mmol) of tetrakis(triphenylphosphine)palladium(0), and the mixture was stirred at 80° C. for 2 hours under a nitrogen stream. After that, the aqueous layer of this mixture was subjected to extraction with toluene, and the obtained solution of the extract and the organic layer were combined and washed with saturated brine. The organic layer was dried with magnesium sulfate, and this mixture was gravity-filtered. An oily substance obtained by concentration of the obtained filtrate was purified by silica gel column chromatography (a developing solvent in which the ratio of hexane to toluene was 19:1) to give a white solid. The obtained solid was recrystallized with a mixed solvent of toluene and hexane, so that 0.95 g of white needle-like crystals of the object of the synthesis were obtained in 56% yield. The reaction scheme is illustrated in (R-1).

[Chemical Formula 36]

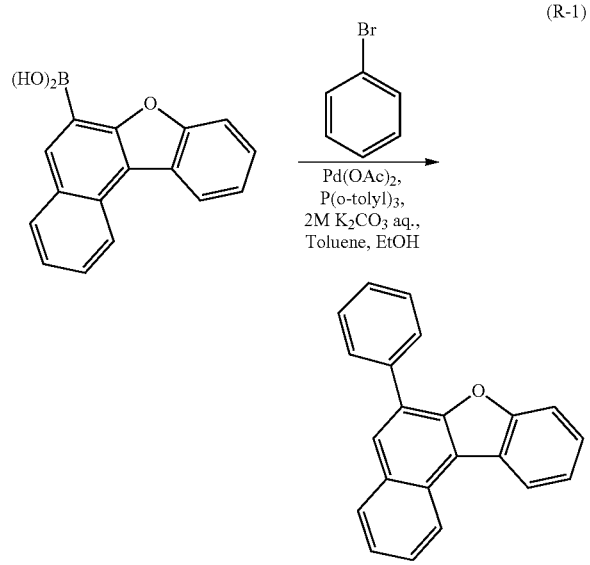

Figure 2:
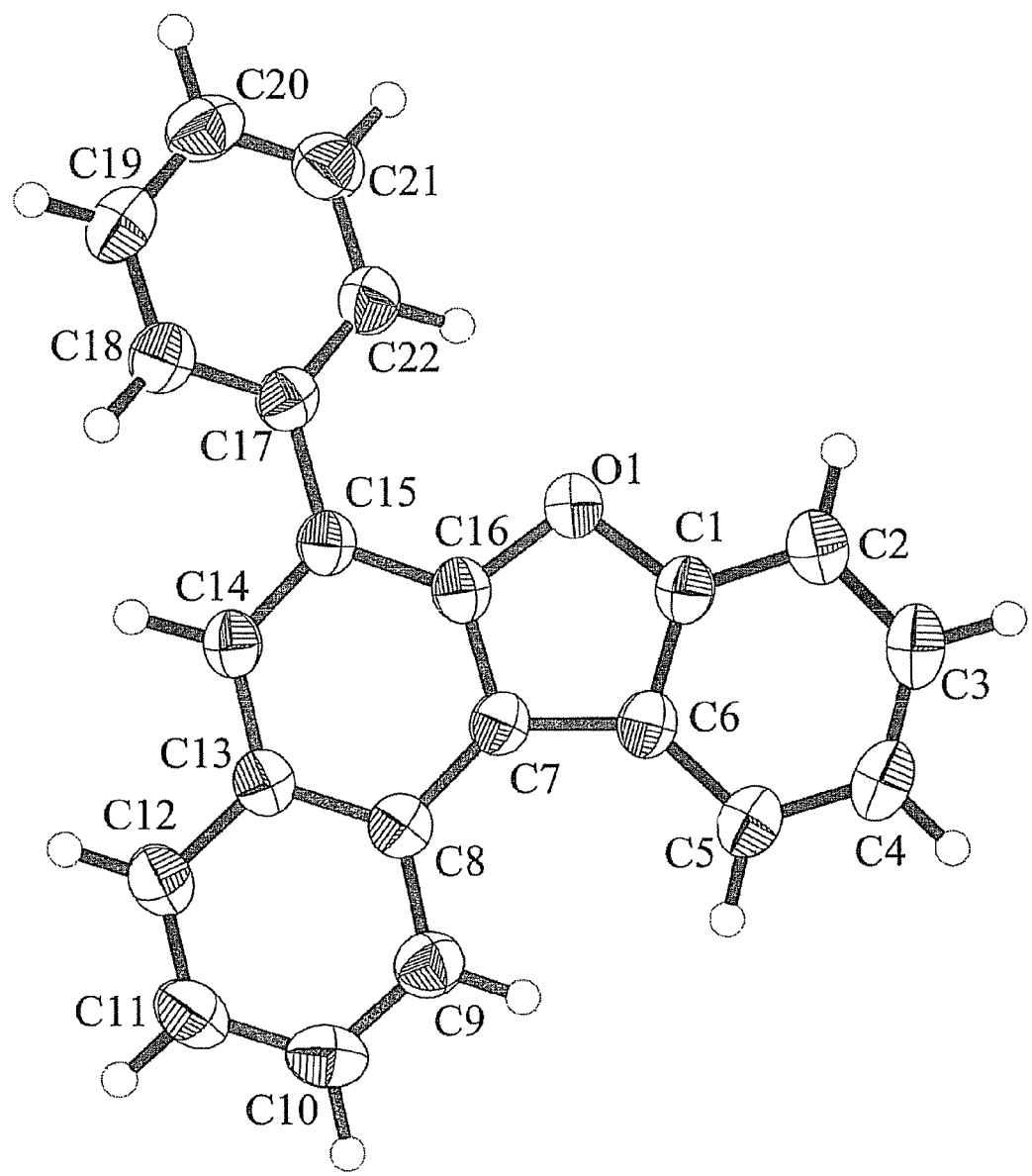
FIG. 2 shows a result of X-ray crystallography of PBnf (abbreviation).

A result of the X-ray crystallography of the obtained white needle-like crystals is shown in FIG. 2. FIG. 2 is an ORTEP (oak ridge thermal ellipsoid plot) drawing. It was confirmed from FIG. 2 that PBnf, which was the object of the synthesis, was obtained. Accordingly, it was shown that the 6-position of benzo[b]naphtho[1,2-d]furan was selectively converted into boronic acid in the reaction scheme (E1-3) and benzo[b]naphtho[1,2-d]furan-6-boronic acid of the object of the synthesis was synthesized.

Reference Example 2

In this reference example, an example in which 6-[3-(9,10-diphenyl-2-anthryl)phenyl]-benzo[b]naphtho[1,2-d]furan (abbreviation: 2mBnfPPA) represented by Structural Formula (300) below is synthesized using the benzo[b]naphtho[1,2-d]furan-6-boronic acid synthesized in Example 1 as a material is described.

[Chemical Formula 37]

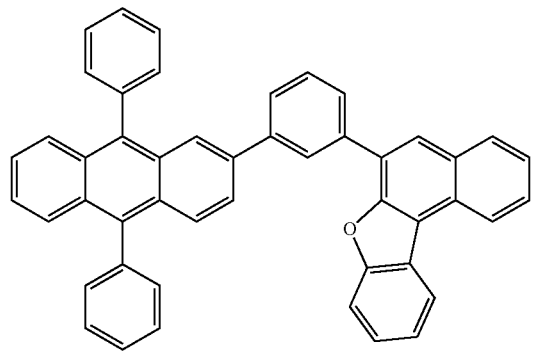

(300)

Synthesis of 6-[3-(9,10-Diphenyl-2-anthryl)phenyl]-benzo[b]naphtho[1,2-d]furan (abbreviation: 2mBnfPPA)

Into a 50 mL three-neck flask were placed 1.1 g (2.4 mmol) of 2-(3-bromophenyl)-9,10-diphenylanthracene, and 0.63 g (2.4 mmol) of benzo[b]naphtho[1,2-d]furan-6-boronic acid, and the air in the flask was replaced with nitrogen. To this mixture were added 10 mL of toluene, 4.0 mL of ethanol, and 3.0 mL of an aqueous solution of sodium carbonate (2.0 mol/L). While the pressure was reduced, this mixture was stirred to be degassed. To this mixture was added 0.14 g (0.12 mmol) of tetrakis(triphenylphosphine)palladium(0), and the mixture was stirred at 80° C. for 3 hours under a nitrogen stream. After that, the aqueous layer of this mixture was subjected to extraction with toluene, and the obtained solution of the extract and the organic layer were combined and washed with saturated brine. The organic layer was dried with magnesium sulfate, and this mixture was gravity-filtered. An oily substance obtained by concentration of the obtained filtrate was purified by silica gel column chromatography (a developing solvent in which the ratio of hexane to toluene was 5:1) to give an oily substance. The obtained oily substance was recrystallized with a mixed solvent of toluene and hexane, so that 1.0 g of a pale yellow powder of the object of the synthesis was obtained in 66% yield.

By a train sublimation method, 1.0 g of the obtained pale yellow powder solid was purified. In the sublimation purification, the pale yellow powder solid was heated at 290° C. under a pressure of 2.2 Pa with a flow rate of argon at 5.0 mL/min. After the sublimation purification, 0.91 g of a pale yellow solid of 2mBnfPPA was recovered in 91% yield. The synthesis scheme is illustrated in (R-2).

[Chemical Formula 38]

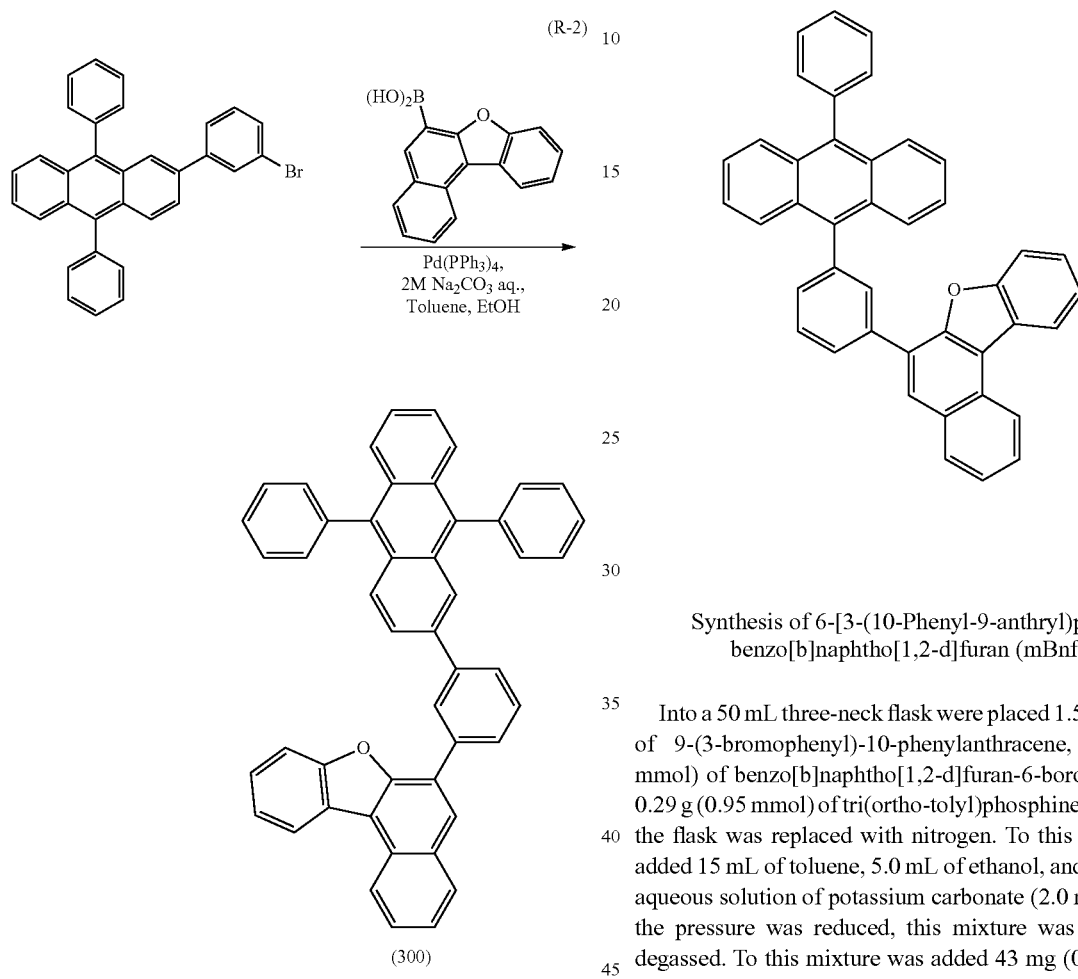

Nuclear magnetic resonance (NMR) spectroscopy identified this compound as 6-[3-(9,10-diphenyl-2-anthryl)phenyl]-benzo[b]naphtho[1,2-d]furan (abbreviation: 2mBnfPPA), which was the object of the synthesis.

$^1$H-NMR measurement data of the obtained compound are as follows: $^1$H-NMR (CDCl$_3$, 300 MHz): δ=7.33 (d, J=3.0 Hz, 1H), 7.35 (d, J=3.0 Hz, 1H), 7.49-7.75 (m, 20H), 7.83 (d, J=9.3z, 1H), 7.94 (d, J=7.5 Hz, 1H), 8.01-8.07 (m, 3H), 8.14 (s, 1H), 8.43-8.47 (m, 1H), 8.66 (d, J$_1$=8.4 Hz, 1H)

Thus, it was confirmed that the organoboron compound represented by General Formula (G1) (specifically, benzo[b]naphtho[1,2-d]furan-6-boronic acid) was able to be used as a synthetic intermediate of another organic compound.

Reference Example 3

In this reference example, an example in which 6-[3-(10-phenyl-9-anthryl)phenyl]-benzo[b]naphtho[1,2-d]furan (abbreviation: mBnfPA) represented by Structural Formula (301) below is synthesized using the benzo[b]naphtho[1,2-d]furan-6-boronic acid synthesized in Example 1 as a material is described.

[Chemical Formula 39]

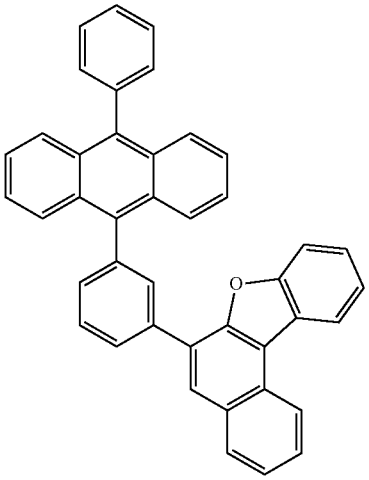

Synthesis of 6-[3-(10-Phenyl-9-anthryl)phenyl]-benzo[b]naphtho[1,2-d]furan (mBnfPA)

Into a 50 mL three-neck flask were placed 1.5 g (3.8 mmol) of 9-(3-bromophenyl)-10-phenylanthracene, 1.0 g (3.8 mmol) of benzo[b]naphtho[1,2-d]furan-6-boronic acid, and 0.29 g (0.95 mmol) of tri(ortho-tolyl)phosphine, and the air in the flask was replaced with nitrogen. To this mixture were added 15 mL of toluene, 5.0 mL of ethanol, and 4.0 mL of an aqueous solution of potassium carbonate (2.0 mol/L). While the pressure was reduced, this mixture was stirred to be degassed. To this mixture was added 43 mg (0.19 mmol) of palladium(II) acetate, and the mixture was stirred at 80° C. for 4 hours under a nitrogen stream. After that, the aqueous layer of this mixture was subjected to extraction with toluene, and the obtained solution of the extract and the organic layer were combined and washed with saturated brine. The organic layer was dried with magnesium sulfate, and this mixture was gravity-filtered. An oily substance obtained by concentration of the obtained filtrate was purified by silica gel column chromatography (a developing solvent in which the ratio of hexane to toluene was 5:1) to give an oily substance. The obtained oily substance was recrystallized with a mixed solvent of toluene and hexane, so that 1.4 g of a white powder of the object of the synthesis was obtained in 67% yield.

By a train sublimation method, 1.1 g of the obtained white powder solid was purified. In the sublimation purification, mBnfPA was heated at 270° C. under a pressure of 2.2 Pa with a flow rate of argon at 5.0 mL/min. After the sublimation purification, 1.0 g of a pale yellow solid of mBnfPA was recovered in 90% yield. The synthesis scheme is illustrated in (R-3).

[Chemical Formula 40]

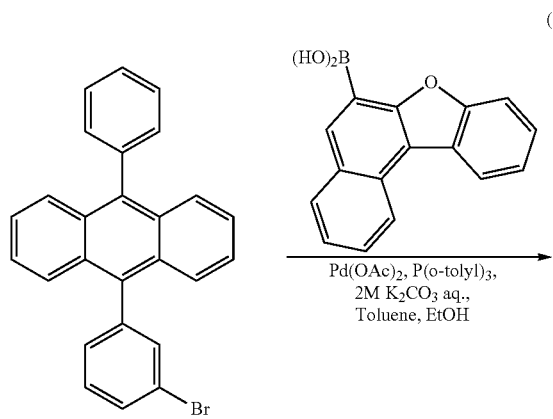

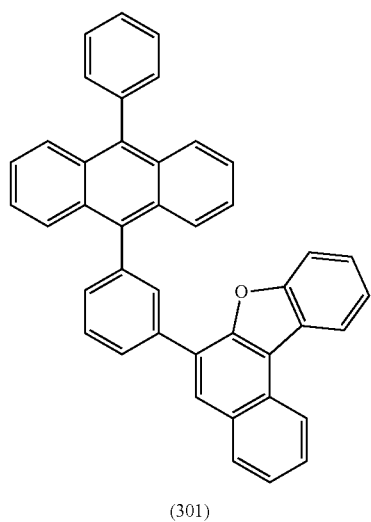

Nuclear magnetic resonance (NMR) spectroscopy identified this compound as 6-[3-(10-phenyl-9-anthryl)phenyl]-benzo[b]naphtho[1,2-d]furan (abbreviation: mBnfPA), which was the object of the synthesis.

$^1$H-NMR measurement data of the obtained compound are as follows: $^1$H-NMR (CDCl$_3$, 300 MHz): δ=7.34-7.44 (m, 4H), 7.48-7.63 (m, 9H), 7.69-7.74 (m, 4H), 7.83 (t, J=7.5 Hz, 1H), 7.96 (dd, J$_1$=1.8 Hz, J$_2$=7.8 Hz, 2H), 8.04 (d, J=7.8 Hz, 1H), 8.13 (s, 1H), 8.15 (t, J=1.5 Hz, 1H), 8.26 (d, J=7.8 Hz, 1H), 8.43-8.46 (m, 1H), 8.66 (d, J=7.8 Hz, 1H)

Thus, it was confirmed that the organoboron compound represented by General Formula (G1) (specifically, benzo[b]naphtho[1,2-d]furan-6-boronic acid) was able to be used as a synthetic intermediate of another organic compound.

Example 2

In this example, a synthesis example in which benzo[b]naphtho[1,2-d]thiophene-6-boronic acid represented by Structural Formula (200) in Embodiment 1 is manufactured is described.

[Chemical Formula 41]

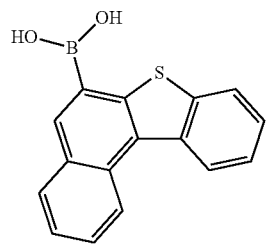

Into a 100 mL three-neck flask was placed 1.0 g (4.2 mmol) of benzo[b]naphtho[1,2-d]thiophene, and the air in the flask was replaced with nitrogen. Into the flask, 20 mL of tetrahydrofuran (THF) was added, and this mixture was cooled to −80° C. Then, 3.0 mL (4.8 mmol) of n-butyllithium (a 1.6 mol/L hexane solution) was dripped into this mixture with a syringe. After that, the mixture was stirred for 2 hours while the temperature was increased to room temperature. Then, this mixture was again cooled to −80° C., and 1.1 mL (10 mmol) of trimethyl borate was added to this mixture. This solution was stirred for 18 hours while its temperature was returned to room temperature. After that, about 50 mL of dilute hydrochloric acid (1.0 mol/L) was added to this mixture, and the mixture was stirred for 1 hour. After that, the aqueous layer of this mixture was subjected to extraction with ethyl acetate, and the obtained solution of the extract and the organic layer were combined and washed with a saturated aqueous solution of sodium hydrogen carbonate and saturated brine. The organic layer was dried with magnesium sulfate, and this mixture was gravity-filtered. The obtained filtrate was concentrated to give a solid. Toluene was added to the obtained solid, the mixture was irradiated with ultrasonic waves, and a solid was collected by suction filtration, so that 0.57 g of a white powder of the object of the synthesis was obtained in 49% yield. The reaction scheme is illustrated in (E3) below.

[Chemical Formula 42]

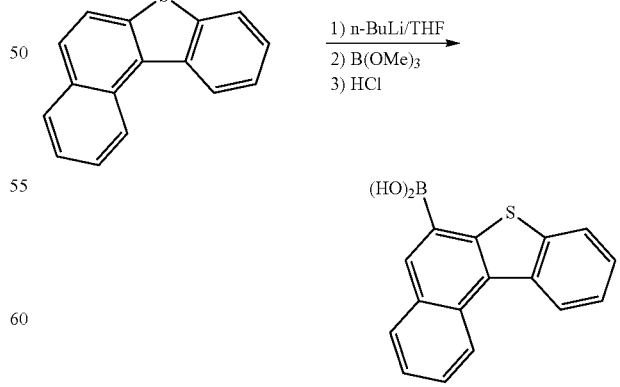

Thus, the benzo[b]naphtho[1,2-d]thiophene-6-boronic acid represented by Structural Formula (200) can be synthesized.

Reference Example 4

In this reference example, an example in which 6-[3-(9,10-diphenyl-2-anthryl)phenyl]-benzo[b]naphtho[1,2-d]thiophene (abbreviation: 2mBntPPA) represented by Structural Formula (400) below is synthesized using the benzo[b]naphtho[1,2-d]thiophene-6-boronic acid synthesized in Example 2 as a material is described.

[Chemical Formula 43]

(400)

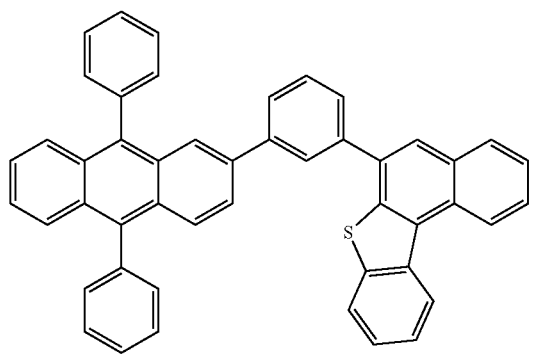

[Chemical Formula 44]

(R-4)

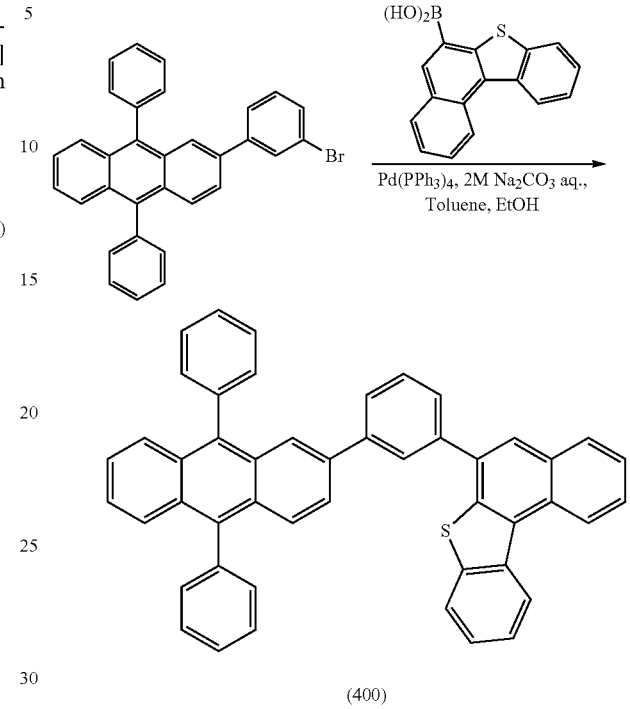

(400)

Into a 50 mL three-neck flask were placed 1.0 g (2.0 mmol) of 2-(3-bromophenyl)-9,10-diphenylanthracene and 0.57 g (2.0 mmol) of benzo[b]naphtho[1,2-d]thiophene-6-boronic acid, and the air in the flask was replaced with nitrogen. To this mixture were added 7.0 mL of toluene, 3.0 mL of ethanol, and 2.0 mL of an aqueous solution of potassium carbonate (2.0 mol/L). While the pressure was reduced, this mixture was stirred to be degassed. To this mixture was added 0.11 g (0.10 mmol) of tetrakis(triphenylphosphine)palladium(0), and the mixture was stirred at 80° C. for 14 hours under a nitrogen stream. After that, the aqueous layer of this mixture was subjected to extraction with toluene, and the obtained solution of the extract and the organic layer were combined and washed with saturated brine. The organic layer was dried with magnesium sulfate, and this mixture was gravity-filtered. The obtained filtrate was concentrated to give an oily substance. The obtained oily substance was purified by silica gel column chromatography (a developing solvent in which the ratio of hexane to toluene was 5:1) to give an oily substance. The obtained oily substance was recrystallized with hexane, so that 0.83 g of a yellow powder of the object of the synthesis was obtained in 64% yield.

By a train sublimation method, 0.83 g of the obtained yellow powder solid was purified. In the sublimation purification, 2mBntPPA was heated at 290° C. under a pressure of 2.8 Pa with a flow rate of argon at 5.0 mL/min. After the sublimation purification, 0.33 g of a pale yellow solid of 2mBntPPA was obtained in 40% yield. The synthesis scheme is illustrated in (R-4).

Nuclear magnetic resonance (NMR) spectroscopy identified this compound as 6-[3-(9,10-diphenyl-2-anthryl)phenyl]-benzo[b]naphtho[1,2-d]thiophene (abbreviation: 2mBntPPA), which was the object of the synthesis.

$^1$H-NMR measurement data of the obtained compound are as follows: $^1$H-NMR (CDCl$_3$, 300 MHz): δ=7.34 (dd, J=7.2 Hz, 3.0 Hz, 2H), 7.45-8.07 (m, 26H), 8.93 (d, j=8.1 Hz, 1H), 9.08 (d, J=8.7 Hz, 1H)

Thus, it was confirmed that the organoboron compound represented by General Formula (G1) which was synthesized in Example 2 (specifically, benzo[b]naphtho[1,2-d]thiophene-6-boronic acid) was able to be used as a synthetic intermediate of another organic compound.

This application is based on Japanese Patent Application serial no. 2010-292993 filed with the Japan Patent Office on Dec. 28, 2010, the entire contents of which are hereby incorporated by reference.

The invention claimed is:

1. An organoboron compound represented by a general formula (G1):

(G1)

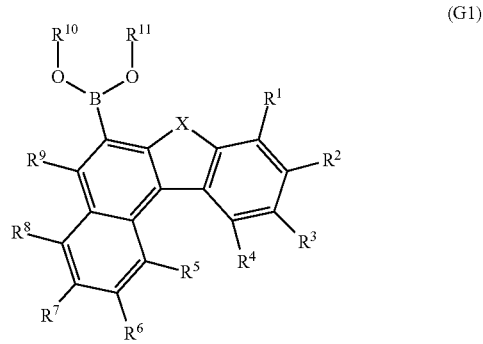

wherein, in the general formula (G1):

the R1 to R8 separately represent any one of hydrogen, an alkyl group having 1 to 6 carbon atoms, and an aryl group having 6 to 16 carbon atoms;

the R9 represents hydrogen or an alkyl group having 1 to 6 carbon atoms;

the R10 and R11 separately represent hydrogen or an alkyl group having 1 to 6 carbon atoms; and the X represents an oxygen atom or a sulfur atom.

2. A method for synthesizing an organoboron compound represented by a general formula (G1), comprising the step of converting a benzo[b]naphtho[1,2-d]furan compound or a benzo[b]naphtho[1,2-d]thiophene compound into organoboron with use of an alkyllithium reagent and a boron reagent,

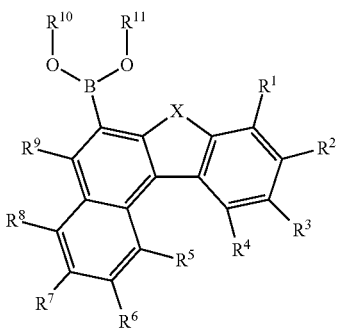

(G1)

wherein, in the general formula (G1):

the R1 to R9 separately represent any one of hydrogen, an alkyl group having 1 to 6 carbon atoms, and an aryl group having 6 to 16 carbon atoms;

the R10 and R11 separately represent hydrogen or an alkyl group having 1 to 6 carbon atoms; and the X represents an oxygen atom or a sulfur atom.

3. The organoboron compound according to claim 1, wherein the organoboron compound is represented by a general formula (G2)

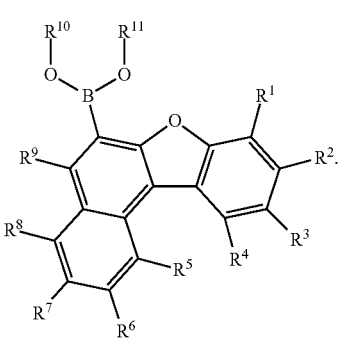

(G2)

4. The organoboron compound according to claim 1, wherein the organoboron compound is represented by a general formula (G3)

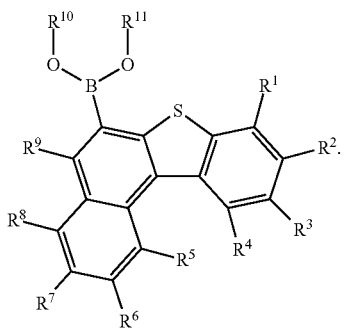

(G3)

5. The organoboron compound according to claim 1, wherein the organoboron compound is represented by a chemical formula (100)

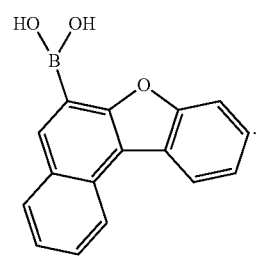

(100)

6. An organoboron compound represented by a general formula (G1):

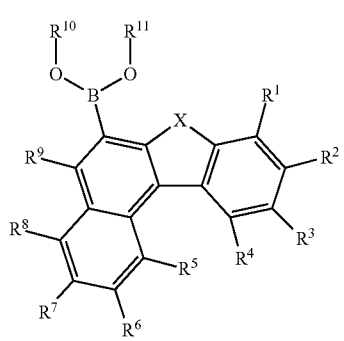

(G1)

wherein, in the general formula (G1):

the R1 to R8 separately represent any one of hydrogen, an alkyl group having 1 to 6 carbon atoms, and an aryl group having 6 to 16 carbon atoms;

the R9 represents hydrogen or an alkyl group having 1 to 6 carbon atoms;

the R10 and R11 bonded to each other to form a ring represented by a cyclopentyl group or a cyclohexyl group; and the X represents an oxygen atom or a sulfur atom.

7. The organoboron compound according to claim 6, wherein the organoboron compound is represented by a general formula (G1-1)

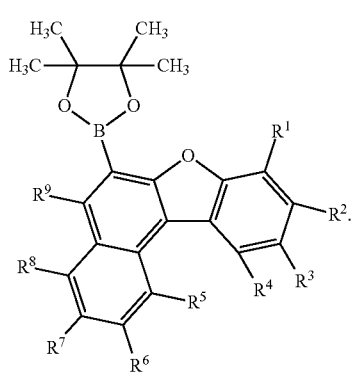
(G1-1)

8. The organoboron compound according to claim 6, wherein the organoboron compound is represented by a general formula (G1-2)

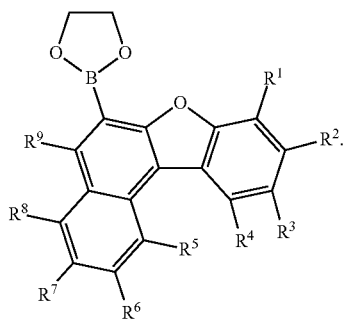
(G1-2)

9. The organoboron compound according to claim 6, wherein the organoboron compound is represented by a general formula (G1-3)

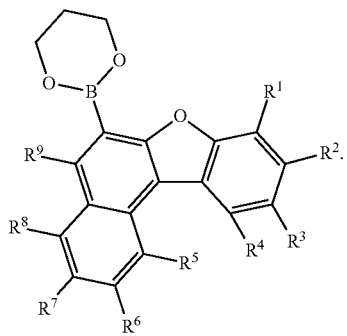
(G1-3)

10. A method for synthesizing an organoboron compound represented by a general formula (G1), comprising the step of converting a benzo[b]naphtho[1,2-d]furan compound or a benzo[b]naphtho[1,2-d]thiophene compound into organoboron with use of an alkyllithium reagent and a boron reagent,

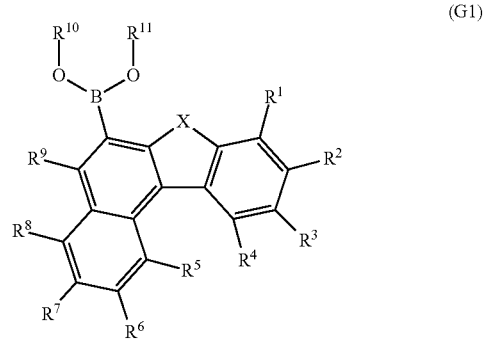
(G1)

wherein, in the general formula (G1):

the R1 to R9 separately represent any one of hydrogen, an alkyl group having 1 to 6 carbon atoms, and an aryl group having 6 to 16 carbon atoms;

the R10 and R11 bonded to each other to form a ring represented by a cyclopentyl group or a cyclohexyl group; and the X represents an oxygen atom or a sulfur atom.

11. The method for synthesizing an organoboron compound according to claim 2, wherein the benzo[b]naphtho[1,2-d]furan compound or the benzo[b]naphtho[1,2-d]thiophene compound can be obtained by intramolecularly cyclization of a β-naphthol derivative having a halogen group.

12. The method for synthesizing an organoboron compound according to claim 11, wherein the β-naphthol derivative having the halogen group can be obtained by coupling a β-naphthol derivative with an aryl derivative.

13. The method for synthesizing an organoboron compound according to claim 10, wherein the benzo[b]naphtho[1,2-d]furan compound or the benzo[b]naphtho[1,2-d]thiophene compound can be obtained by intramolecularly cyclization of a β-naphthol derivative having a halogen group.

14. The method for synthesizing an organoboron compound according to claim 13, wherein the β-naphthol derivative having the halogen group can be obtained by coupling a β-naphthol derivative with an aryl derivative.

15. An organoboron compound represented by a general formula (G1):

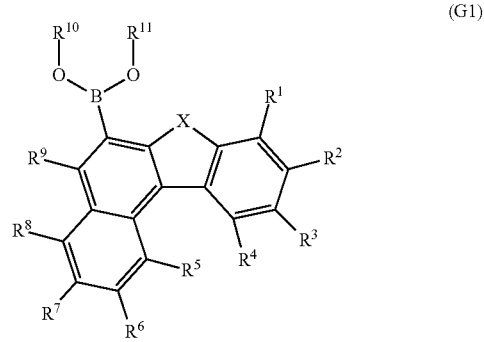
(G1)

wherein, in the general formula (G1):
the R1 to R9 separately represent any one of hydrogen, an alkyl group having 1 to 6 carbon atoms, and an aryl group having 6 to 16 carbon atoms;
the R10 and R11 separately represent an alkyl group having 1 to 6 carbon atoms; and
the X represents an oxygen atom or a sulfur atom.

* * * * *